US008227606B2

(12) United States Patent
Jia et al.

(10) Patent No.: US 8,227,606 B2
(45) Date of Patent: Jul. 24, 2012

(54) ARGININE DERIVATIVES WITH NP-1 ANTAGONISTIC ACTIVITY

(75) Inventors: Haiyan Jia, London (GB); Ian Zachary, London (GB); Michelle Tickner, London (GB); Lili Cheng, London (GB); Chris Chapman, London (GB); Katie Ellard, London (GB); Basil Hartzoulakis, London (GB); Ashley Jarvis, London (GB); Rosemary Lynch, London (GB); Jamie Nally, London (GB); David Selwood, London (GB); Mark Stewart, London (GB)

(73) Assignee: Ark Therapeutics, Ltd., London (GB)

( * ) Notice: Subject to any disclaimer, the term of this patent is extended or adjusted under 35 U.S.C. 154(b) by 0 days.

(21) Appl. No.: 13/361,134

(22) Filed: Jan. 30, 2012

(65) Prior Publication Data
US 2012/0122862 A1 May 17, 2012

Related U.S. Application Data

(62) Division of application No. 12/439,523, filed as application No. PCT/GB2007/003766 on Oct. 4, 2007, now Pat. No. 8,158,789.

(30) Foreign Application Priority Data

Oct. 4, 2006 (GB) .................................. 0619611.7

(51) Int. Cl.
*C07D 417/14* (2006.01)

(52) U.S. Cl. ...................................................... 544/369
(58) Field of Classification Search .................. 544/369
See application file for complete search history.

(56) References Cited

FOREIGN PATENT DOCUMENTS

| EP | 0477049 A1 | 3/1992 |
| EP | 0825194 A2 | 2/1998 |
| WO | WO98/57931 | 12/1998 |
| WO | WO03/082918 A1 | 10/2003 |
| WO | WO2005/012288 A1 | 2/2005 |
| WO | WO2005/123686 A1 | 12/2005 |
| WO | WO2006/040279 A1 | 4/2006 |
| WO | WO2006/052722 A1 | 5/2006 |

OTHER PUBLICATIONS

Neustadt, B.R., et al., "Construction of a Family of Biphenyl Combinatorial Libraries: Structure-Activity Studies Utilizing Libraries of Mixtures," Bioorganic & Medicinal Chemistry Letters (1998) 8, 2395-2398.
Vazquez, E., et al., "An Fmoc Solid-Phase Approach to Linear Polypyrrole-Peptide Conjugates," Tetrahedron Letters (1999) 40, 3621-3624.
Jarvis, A., et al., "Small Molecule Inhibitors of the Neuropilin-1 Vascular Endothelial Growth Factor A (VEGF-A) Interaction," J. Med. Chem (2010) 53, 2215-2226. (Does not qualify as prior art.).
Podlipskii, V., et al., Doklady Akademii Nauk Ukrainskoi SSR, Seriya B: Geoogicheskie, (1989) 8, 46-49. (Not in English.).
Gershkovich, A., et al., Urkrainskii Biokhimicheskii Zhurnal, (1995) 67(1), 57-64. (Not in English.).

*Primary Examiner* — Taofiq A Solola
(74) *Attorney, Agent, or Firm* — Pharmaceutical Patent Atty's, LLC

(57) ABSTRACT

The present invention is a compound of formula (I) or formula (II) which are suitable as NP-1 antagonists.

14 Claims, No Drawings

ARGININE DERIVATIVES WITH NP-1 ANTAGONISTIC ACTIVITY

RELATED APPLICATIONS

This application is a divisional application of U.S. application Ser. No. 12/439,523, filed on Sep. 15, 2009 now U.S. Pat. No. 8,158,789; which is a National Stage Application of International Application No. PCT/GB2007/003766, filed Oct. 4, 2007; which claims priority from Great Britain Application Serial No. 0619611.7, filed Oct. 4, 2006; all of which are incorporated herein by reference in their entirety.

FIELD OF THE INVENTION

This invention relates to peptidomimetics which have NP-1 antagonist activity and which have activity of potential benefit in therapy.

BACKGROUND OF THE INVENTION

A non-tyrosine kinase transmembrane protein, neuropilin-1 (NP-1) is a receptor for members of the VEGF family of angiogenic cytokines, particularly VEGF-$A_{165}$, as wells as a receptor for a family of molecules called semaphorins or collapsins which play a key role in the guidance of neuronal axons during mammalian development. In particular, NP-1 is known to mediate the growth cone-collapsing and chemorepulsive activity of semaphorin 3A. NP-1 has been shown to play a role in the primary T-cell immune response.

There are a number of conditions in which NP-1 may have a significant role in pathology. Such conditions include stroke, ischaemic eye disease, cancer and rheumatoid arthritis.

SUMMARY OF THE INVENTION

New compounds have been discovered, which have NP-1 antagonist activity.

According to a first aspect, the present invention is a compound of formula I or formula II

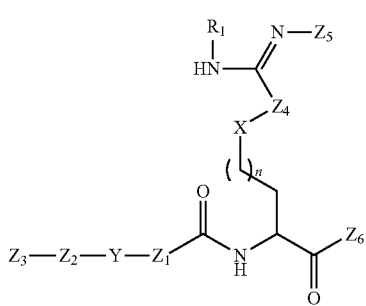

(I)

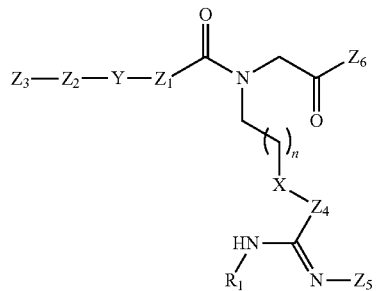

(II)

wherein
$X$ is $CH_2$, $C(O)$, $NH$, $O$ or $SO_2$;
$Y$ is a direct bond or furanylene;
$Z_1$ is an arylene or heteroaromatic group;
$Z_2$ is a direct bond, a $SO_2NH$, $CONH$ or $NHCONH$ group;
$Z_3$ is an aryl or heteroaromatic group;
$Z_4$ is $CH_2$ or $NR_1$;
$Z_5$ is H, OH, $C(O)OR_1$ or $P(O)(OR_1)_2$;
$Z_6$ is, $OR_1$ or $NHR_2$;
each $R_1$ is independently H or an alkyl group;
each $R_2$ is independently H or a CN, OH or $SO_2CH_3$ group; and
n is 0, 1 or 2,
or a pharmaceutically acceptable salt, solvate or polymorph thereof.

DESCRIPTION OF PREFERRED EMBODIMENTS

Preferably, the compound is of formula I, wherein X, Y, $Z_{1-6}$, and $R_{1-2}$ are as defined above.

It will be appreciated that the compounds according to the invention contain an asymmetrically substituted carbon atom. The presence of this asymmetric centre in a compound of formula (I) can give rise to stereoisomers, and in each case the invention is to be understood to extend to all such stereoisomers, including enantiomers and diastereomers, and mixtures including racemic and non-racemic mixtures thereof.

It will also be appreciated that tautomers of the specific compounds of the invention exist, and these are included within the scope of the invention. These tautomers may be formed after the formal migration of a hydrogen atom, and the switch of a single bond and an adjacent double band. Methods of tautomerization will be well known to those skilled in the art.

As used in this specification, alone or in combination, the term "alkyl" refers to a straight or branched chain alkyl moiety, including for example, methyl, ethyl, propyl, isopropyl, butyl, tert-butyl, pentyl, hexyl and the like.

The term "aryl" means an aromatic hydrocarbon moiety and includes phenyl, biphenyl or naphthyl group. The aryl ring may be substituted, for example by an $NO_2$ group.

The term "arylene" means a divalent aromatic hydrocarbon moiety and includes phenylene, biphenylene or naphthylene. The arylene ring may be substituted, for example by an $NH_2$ group.

The term "heteroaromatic" refers to monovalent or divalent aromatic ring systems, from which at least one ring atom is selected from the group, O, N, or S and includes for example benzofused furanyl, thiophenylene, thiophenylene (phenyl), pyridyl, indolyl, pyridazinyl, piperazinyl, pyrimidinyl, thiazolylene and the like.

The activity of the compounds of the invention means that they may be useful in the treatment of diseases in which NP-1 may have a significant role in pathology. The compounds of the invention may be useful for stimulating nerve repair, for the treatment of neurodegeneration and for use in anti-cancer therapy. They may also be useful in the treatment of a disease where modulation of the immune system is required, for example, following transplant surgery. Yet other conditions that may be treated using a compound of the invention include skin diseases such as psoriasis, diseases requiring immuno-modulation, angiogenesis in the eye, diabetes, macular degeneration, glaucoma and heart failure.

For therapeutic use, compounds of the invention may be formulated and administered by procedures, and using components, known to those of ordinary skill in the art. The appropriate dosage of the compound may be chosen by the skilled person having regard to the usual factors such as the condition of the subject to be treated, the potency of the compound, the route of administration etc. Suitable routes of administration include oral, intravenous, intramuscular, intraperitoneal, intranasal and subcutaneous.

A NP-1 antagonist may compete with semaphorin-3A for binding to NP-1, and thereby antagonise inhibitory effects of semaphorin-3A on axonal outgrowth and migration in nerve cells. Potential applications of this are in promoting neurite outgrowth, in stimulating nerve repair or treating neurodegeneration. Further, an NP-1 antagonist may promote the survival of semaphorin-3A-responsive neurones, an effect that would confirm or enhance its utility in the applications given above, and may extend these applications, e.g. to treating neuronal death caused by episodes of ischaemia as in stroke and some eye diseases.

Recent evidence suggests a role for NP-1 in angiogenesis. The evidence shows that NP-1 may be essential for VEGF-induced angiogenesis in cancer, eye disease, rheumatoid arthritis and other diseases. Therefore, NP-1 antagonists may have applications in the inhibition of VEGF-dependent angiogenesis in disease.

NP-1 antagonists may also play a role in modulating the immune system. Therefore, it may be useful to give a compound of the invention before, during or after a transplant.

In addition, a NP-1 antagonist may compete with VEGF for binding to NP-1 in tumour cells and promote cell death in NP-1-expressing tumour cells. Potential applications of this are in anti-cancer therapy. Furthermore, a NP-1 antagonist has anti-metastatic potential since it effectively inhibits carcinoma cell adhesion to extra-cellular matrix proteins and cell migration.

The following examples illustrate the invention. General schemes for synthesising peptidomimetics of the invention are provided. Experimental detail, for both the solid and solution phase experiments, is also given.

ABBREVIATIONS

Ar; aromatic, Arg, Arginine; Boc, tert-butoxy carbonyl; Trt, trityl; tBu, tert-butyl; Acm, acetamidomethyl; DIC, diisopropylcarbodiimide; DIPEA, N,N-diisopropylethylamine, Et, ethyl; Fmoc, 9-fluorenylmethoxy-carbonyl; HATU, 2-(7-aza-1H-benzotriazole-1-yl)-1,1,3,3-tetramethyluronium hexafluorophosphate; HBTU, 2-(1H-benzotriazol-1-yl)-1,1,3,3-tetramethyluronium hexafluorophosphate; HetAr; Heteroaromatic, HOBt, 1-hydroxybenzotriazole; HPLC, high performance liquid chromatography; LC-MS, liquid chromatography mass spectrometry; Me, methyl; Pbf, 2,2,4,6,7-pentamethyldihydrobenzofuran-5-sulfonyl; PG, protecting group; py, pyridine; PyBrOP, bromo-tris-pyrrolidino-phosphonium hexafluorophosphate; THF, tetrahydrofuran; TLC, thin-layer chromatography.

Solid Phase

Definitions and Final Compound Characterisation

General Procedure for the Synthesis of Sulfonamides

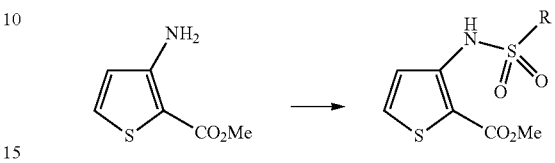

Methyl-3-aminothiophene-2-carboxylate (100-500 mg, 1 eq) was stirred with the corresponding aromatic sulfonyl chloride (1.1 eq) in pyridine (5 mL), under nitrogen, at 20° C. for 18 hours.

The reaction was monitored using TLC and, after this time, water was added to the reaction mixture (approx. 1 mL) and the solvents removed in vacuo. The resulting red/pink coloured solids were partitioned between 1M hydrochloric acid (aqueous solution, 20 mL) and ethyl acetate (20 mL). The phases were separated and the aqueous phase extracted with ethyl acetate (3×20 mL). The organic phases were combined and washed with water (25 mL), brine (saturated aqueous solution, 25 mL), dried over magnesium sulfate, filtered and the solvent removed in vacuo to typically afford a red/brown oily solid. The solid was then purified using flash column chromatography on silica gel (eluent ethyl acetate: iso-hexane; 25:75.

Bromo-tris-pyrrolidino-phosphonium hexafluorophosphate (1 eq) was added to a stirred solution of the aniline (1.5 mmol, 1 eq), the free acid (1.5 mmol, 1 eq) and N,N-diisopropylethylamine (3 eq) in acetonitrile (5 mL). The reaction mixture was then stirred for 20 h at 85° C. After this time the reaction solvent was removed in vacuo and the residue dissolved in ethyl acetate (15 mL).

General Procedure for the Reaction of Thiophene Amino Acids with Sulfonyl Chlorides

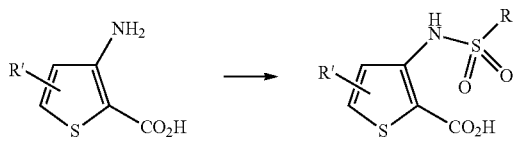

The amine (1 eq) was dissolved in 1,4-dioxane (7.5 mL), sodium carbonate (5 eq) was dissolved in water (7.5 mL) and the two solutions combined and stirred vigorously. Sulfonyl chloride (1.5-2.5 eq) was added, portionwise over one hour, and the brown reaction mixture stirred at room temperature for 48 hours. After this time the reaction solvent was reduced to half the volume and diluted with water (15 ml). This phase was washed with diethyl ether (15 mL) and then acidified with potassium hydrogen sulfate (10% aqueous solution). The resultant precipitate was extracted into ethyl acetate, the phases separated and the solvent removed in vacuo to afford a brown semi-solid which was purified using flash column chromatography on silica gel (eluent:ethyl acetate:iso-hexane; 50:50 increasing to methanol/ethyl acetate; 10:90) to afford the desired compound.

Ester Building Blocks/Intermediates: General Procedure for Solution-Phase PyBroP Coupling

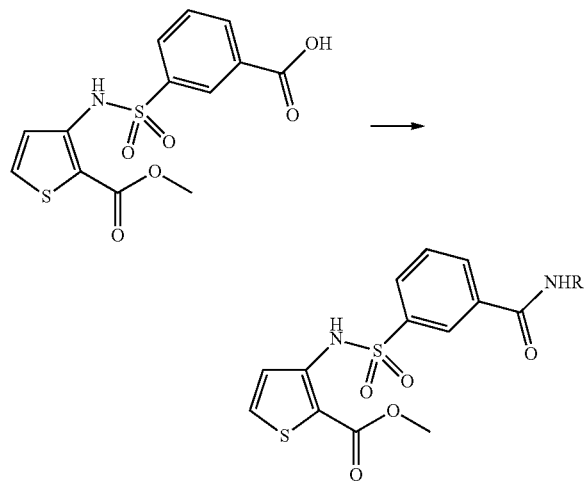

Carboxylic acid (20-250 mg, 1 eq) and bromo-tris-pyrrolidino-phosphonium hexafluorophosphate (1.1 eq) were suspended in dichloromethane (5 mL) and the mixture was stirred at 20° C. for 10 minutes. N,N-Diisopropylethylamine (7 eq) was added to the mixture and stirred for a further 10 minutes. The appropriate amine (1.1 eq) was added and the reaction mixture was then stirred for 24-48 hours at 20° C. After this time the reaction solvent was removed in vacuo and the residue partitioned between hydrochloric acid (1M aqueous solution, 20 mL) and ethyl acetate (20 mL). The phases were separated and the aqueous phase extracted with ethyl acetate (3×20 mL). The organic phases were combined and washed with brine (saturated, aqueous solution, 25 mL), dried over magnesium sulfate, filtered and the solvent removed in vacuo to afford the crude residue.

General Procedure for Removal of the Fmoc Group from Fmoc-Arg-Wang Resin

The Fmoc-Arg-Wang resin (typically 100 mg, 1 eq) was swollen with N,N-dimethylformamide (2 mL) for 30 minutes. The N,N-dimethylformamide was removed, piperidine in N,N-dimethylformamide (2 mL, 1:5) was added and the resin agitated for 5 minutes. The solvent was removed, and further piperidine in N,N-dimethylformamide (2 mL, 1:5) was added and agitated for a further 15 minutes. The solvents were removed and the resin was washed with dichloromethane (5 mL), methanol (5 mL), N,N-dimethylformamide (5 mL) and dried in vacuo. A Kaiser test was performed and, if positive (i.e., free amine present), the resin was deemed suitable for further transformation.

General Procedure for Coupling of Carboxylic Acid Scaffolds to Arg-Wang Resin

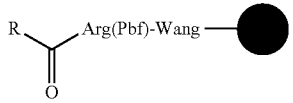

Method A (DIC/HOBt)

The scaffold (3 eq), 1-hydroxybenzotriazole hydrate (3 eq) and N,N'-diisopropylcarbodiimide (3 eq) were dissolved in N,N-dimethylformamide (2 mL) and added to the resin. The reaction mixture was agitated for 3 hours at room temperature, however, some scaffolds were agitated for 18 hours. The reagents were removed from the resin and the resin was washed with dichloromethane (5 mL), methanol (5 mL), and N,N-dimethylformamide (5 mL). A Kaiser test was performed and, if negative (i.e., no free amine present), the resin was deemed suitable for further transformation.

Method B (HBTU/HOBt/DIPEA)

The scaffold (3 eq), 1-hydroxybenzotriazole hydrate (3 eq), and 2-(1H-benzotriazole-1-yl)-1,1,3,3-tetramethyluronium hexafluorophosphate (3 eq) were dissolved in N,N-dimethylformamide (2 mL) and added to the resin. N,N-diisopropylethylamine (9 eq) was added and the reaction mixture was agitated for 3 hours at room temperature, however, some scaffolds were agitated for 18 hours. The reagents were removed from the resin and the resin was washed with dichloromethane (5 mL), methanol (5 mL), and N,N-dimethylformamide (5 mL). A Kaiser test was performed and, if negative (i.e., no free amine present), the resin was deemed suitable for further transformation.

Method C (PyBrOP/DIPEA)

The scaffold (3 eq), bromo-tris-pyrrolidino-phosphonium hexafluorophosphate (4 eq) were dissolved in N,N-dimethylformamide (2 mL) or dichloromethane/N-methyl-2-pyrrolidone (2 mL, 19:1) and added to the resin. N,N-diisopropylethylamine (9 eq) was added and the reaction mixture was agitated for 3 hours at room temperature, however, some scaffolds were agitated for 18 hours. The reagents were removed from the resin and the resin was washed with dichloromethane (5 mL), methanol (5 mL), and N,N-dimethylformamide (5 mL). A Kaiser test was performed and, if negative (i.e., no free amine present), the resin was deemed suitable for further transformation. The resulting resins were dried under vacuum prior to deprotection/cleavage.

General Procedure for the Synthesis of Sulfonamides on the Solid-Phase

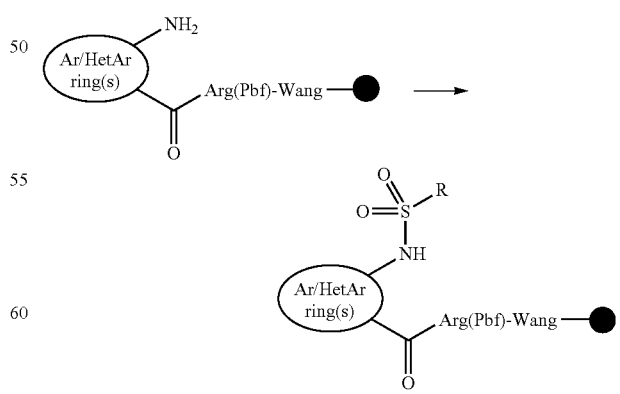

The N-terminal aniline resin (typically 100 mg, 1 eq) was washed with dichloromethane (3×5 mL), 4-nitrobenzene sulfonyl chloride (5 eq) was added in anhydrous dichloromethane (2 mL) followed by triethylamine (3 eq). The reaction mixture was then agitated for 16 hours at room temperature. The reagents were removed and the resin was washed with dichloromethane (2×5 mL), methanol (2×5 mL) and N,N-dimethylformamide (2×5 mL). A chloranil test was performed and, if negative (i.e., no free aniline present), the resin was deemed suitable for further transformation.

General Procedure for the Synthesis of Ureas on the Solid-Phase

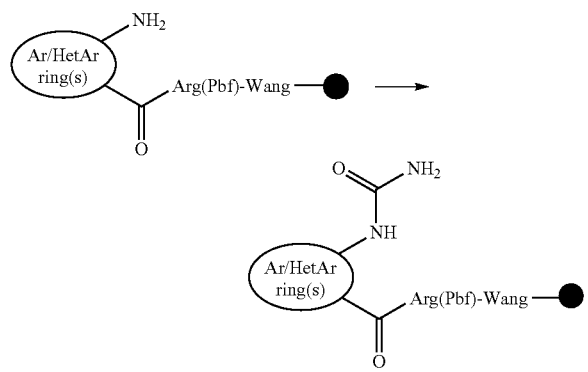

The N-terminal aniline resin (typically 100 mg, 1 eq) was washed with dichloromethane (3×5 mL), 4-nitrophenyl isocyanate (5 eq) was added in dichloromethane (2 mL) and the reaction mixture agitated for 16 hours at room temperature. After this time the reagents were removed and the resin was washed with dichloromethane (2×5 mL), methanol (2×5 mL) and N,N-dimethylformamide (2×5 mL). A chloranil test was performed and, if negative (i.e., no free aniline present), the resin was deemed suitable for further transformation.

General Procedure for Coupling of Acids to Resin Bound Aniline Compounds

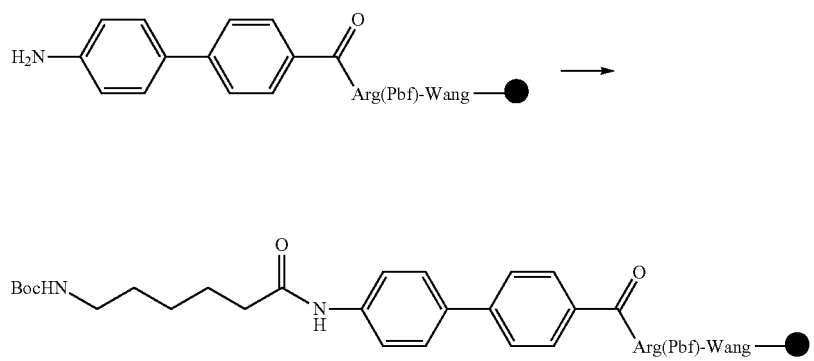

The aniline resin (typically 100 mg, 1 eq) was swollen in the minimum quantity of dichloromethane for 20 minutes, meanwhile the acid (4 eq), bromo-tripyrrolidino-phosphonium-hexafluorophosphate (4.8 eq) and 2,6 lutidine (15 eq) were stirred at room temperature for 15 minutes and added to the pre-swollen resin. The reaction mixture was then agitated at room temperature for 24 hours to effect coupling and then washed with N,N-dimethylformamide (3×10 ml), N,N-dimethylformamide:N,N-diisopropylethylamine (1:1, 3×10 ml), further N,N-dimethylformamide (3×10 ml), dichloromethane (3×10 ml), methanol (3×10 ml) and diethyl ether (3×10 ml). A chloranil test for anilines was carried out and, if negative (i.e., no free amine present), the resin was deemed suitable for cleavage.

General Procedure for the Reduction of Resin-Bound Aromatic Nitro Compounds

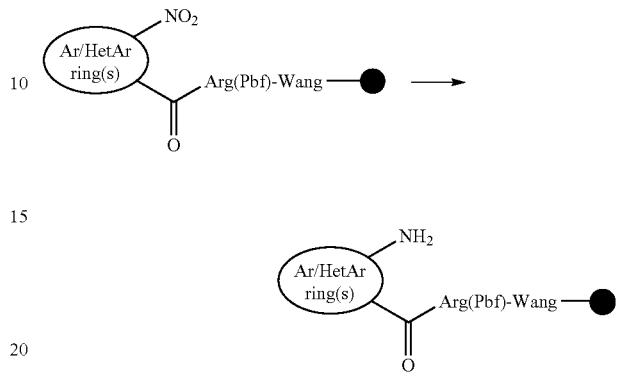

The nitro-containing resin (typically 100 mg, 1 eq) was swollen with N,N-dimethylformamide (2 mL) for 30 minutes. The N,N-dimethylformamide was removed, tin chloride dihydrate (10 eq) was added to the resin in N,N-dimethylformamide (2 mL) and the reaction mixture was agitated for 3 hours followed by 18 hours (with fresh reagents), at room temperature. The reagents were removed and the resin was washed with N,N-dimethylformamide (5 mL), 20% pyridine in N,N-dimethylformamide (5 mL), dichloromethane (5 mL), methanol (5 mL) and N,N-dimethylformamide (5 mL). A chloranil test for anilines was carried out and, if positive (i.e., free amine present), the resin was deemed suitable for cleavage. The resulting resins were dried under vacuum prior to deprotection/cleavage.

General Procedure for Reductive Aminations on the Solid Phase

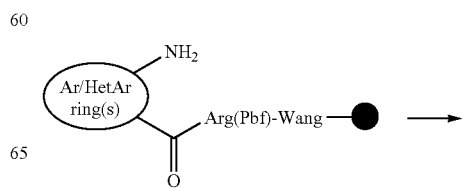

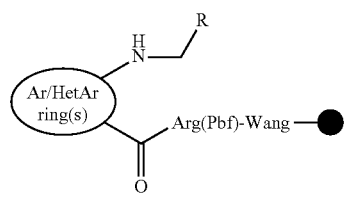

The 3 and 4-aminophenyl containing resin (typically 100 mg, 1 eq) was washed with dichloromethane (2×5 mL). The aldehyde (10 eq) was added to the washed resin in a solution of acetic acid in 1,2-dichloroethane (2 mL, 98:2), the reaction mixture was agitated for 3 hours at 20° C. Sodium triacetoxyborohydride (20 eq) was added and the reaction mixture was agitated for 2 days at 20° C. The reagents were removed and the resin was washed with dichloromethane (2×5 mL), methanol, (2×5 mL), N,N-dimethylformamide (2×5 mL), and dichloromethane (2×5 mL). The resulting resins were dried under vacuum prior to deprotection/cleavage.

General Procedure for Sonogashira Reactions on the Solid Phase

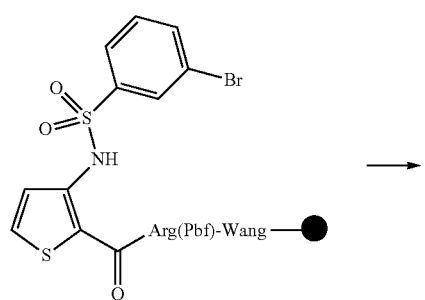

The bromine containing resin (typically 100 mg, 1 eq), alkyne (5 eq) and copper iodide (0.2 eq) were suspended in degassed N,N-dimethylformamide and tetrahydrofuran (5 mL, 1:1). Triethylamine (5 eq) was added, the reaction mixture was further degassed, tetrakis(triphenylphosphine)palladium(0) (0.1 mg) was added and the reaction mixture was stirred for 18 hours at 90° C. After this time the resin was filtered and washed with N,N-dimethylformamide/tetrahydrofuran (1:1, 15 mL), N,N-dimethylformamide/water (2×15 mL), N,N-dimethylformamide (15 mL), dichloromethane (15 mL), methanol (15 mL) and diethyl ether (14 mL). The resulting resins were dried under vacuum prior to deprotection/cleavage.

General Procedure for Suzuki Reactions on the Solid Phase

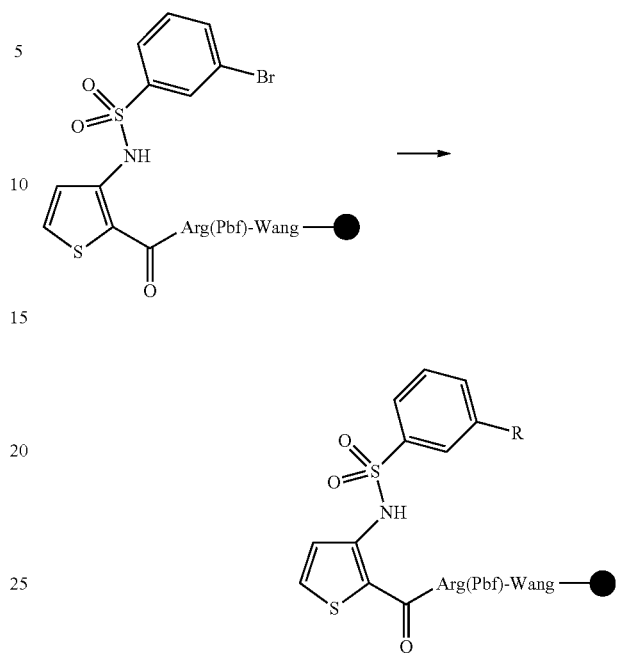

The bromine-containing resin (typically 100 mg, 1 eq), boronic acid (1-5 eq) and sodium carbonate (10 eq, 2M, aqueous solution) were suspended in degassed N,N-dimethylformamide:tetrahydrofuran (1:1, 4 mL). [1,1'-Bis(diphenylphosphino)ferrocene]dichloropalladium(II) (complex with dichloromethane, approx. 5 mg) was added and the solution further degassed. The reaction mixture was gently stirred at 100° C. for 18 hours. After this time the resin was filtered and washed with N,N-dimethylformamide (15 mL), N,N-dimethylformamide/water (15 mL), N,N-dimethylformamide (15 mL), dichloromethane (15 mL), methanol (15 mL) and diethyl ether (14 mL). The resulting resins were dried under vacuum prior to deprotection/cleavage.

General Procedure for Cleaving from Arg-Wang

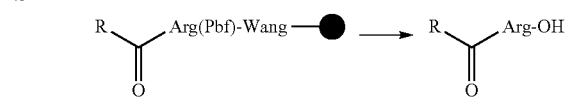

The peptidomimetic resin (approx. 100 mg) was washed thoroughly with dichloromethane (3×5 mL) and dried with nitrogen, then a solution of trifluoroacetic acid (1.9 mL), triisopropyl silane (50 μL) and water (50 μL) was added and the cleavage mixture was agitated for 90 minutes. The cleavage mixture was removed and the resin was further washed with dichloromethane (1 mL). The cleavage/dichloromethane mixtures were combined, further agitated for 90 minutes, and added drop-wise to cold diethyl ether (30 mL, −78° C.). A white solid precipitated and was pelleted by centrifugation, the diethyl ether was decanted and another portion of cold diethyl ether (20 mL) was added, thoroughly mixed, centrifuged, and decanted. This process was repeated once more. The crude final compound was dried under vacuum and purified either by elution through a 2 g C-18 column (eluent: acetonitrile/water) or by (mass-directed) preparative LC-MS using a preparative C-18 column (Phenomenex Gemini, 50×21.2 mm, 5 μm) and a linear AB gradient of 5-95% for B over 15 min at a flow rate of 20 mL/minute, where eluent A was 0.1% formic acid/water and eluent B was 0.1% formic acid/acetonitrile. The purified peptidomimetics were then lyophilized (−54° C., 0.08 mbar) and analysed by reverse-phase LC-MS (analytical C-18 column, Thermo Betabasic, 100×4.6 mm, 5 μm) and an AB gradient of 5-95% for B, over 11 minutes, at a flow rate of 1 mL/minute, where eluent A was 0.1% formic acid/water and eluent B was 0.1% formic acid/acetonitrile.

All final compounds were isolated as trifluoroacetate salts.

Table 1 summarises the final compounds constructed using these methods.

TABLE 1

| ID | EG00136; (S)-2-{[4'-(6-Amino-hexanoylamino)-biphenyl-4-carbonyl]-amino}-5-guanidino-pentanoic acid | EG00144; (S)-2-{[3-(4-Amino-benzenesulfonylamino)-thiophene-2-carbonyl]-amino}-5-guanidino-pentanoic acid |
|---|---|---|
| Structure | | |

| ID | EG00160; (S)-2-{[2-(3-Amino-benzenesulfonylamino)-benzoylamino]-5-guanidino-pentanoic acid | |
|---|---|---|
| Structure | | |

| ID | EG00161; (S)-2-{[2-(4-Amino-benzenesulfonylamino)-benzoylamino]-5-guanidino-pentanoic acid | EG00162; (S)-2-{[2-(3-Amino-benzenesulfonylamino)-benzoylamino]-thiazole-4-carbonyl]-amino}-5-guanidino-pentanoic acid |
|---|---|---|
| Structure | | |

| ID | EG00163; (S)-2-{[5-(2-Amino-phenyl)-furan-2-carbonyl]-amino}-5-guanidino-pentanoic acid | |
|---|---|---|
| Structure | | |

TABLE 1-continued

| ID | EG00164; (S)-2-{[5-(3-Amino-phenyl)-furan-2-carbonyl]-amino}-5-guanidino-pentanoic acid | EG00165; (S)-2-[3-(3-Amino-benzenesulfonylamino)-benzoylamino]-5-guanidino-pentanoic acid |
|---|---|---|
| Structure | 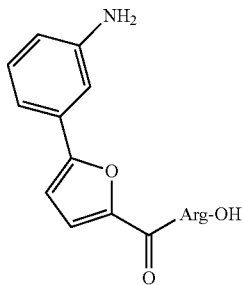 | 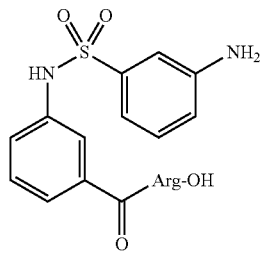 |

| ID | EG00166; (S)-2-[3-(4-Amino-benzenesulfonylamino)-benzoylamino]-5-guanidino-pentanoic acid |
|---|---|
| Structure | 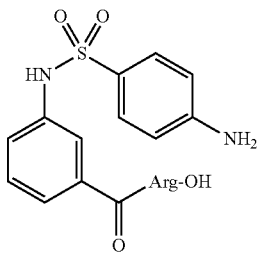 |

| ID | EG00170; (S)-2-({5-[2-(3-Amino-benzenesulfonylamino)-phenyl]-furan-2-carbonyl}-amino)-5-guanidino-pentanoic acid | EG00173; (S)-2-[3-(4-Aminomethyl-benzoylamino)-benzoylamino]-5-guanidino-pentanoic acid |
|---|---|---|
| Structure | 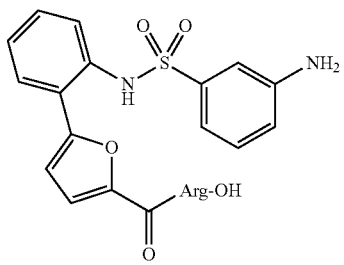 | 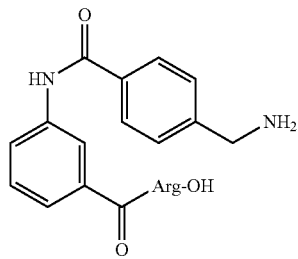 |

| ID | EG00174; (S)-2-{[3-(3-Amino-benzenesulfonylamino)-thiophene-2-carbonyl]-amino}-5-guanidino-pentanoic acid |
|---|---|
| Structure | 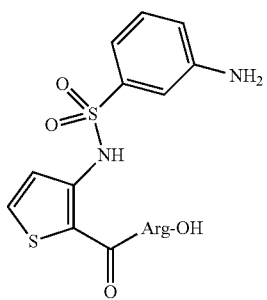 |

TABLE 1-continued

| ID | EG00175; (S)-2-({5-[3-(4-Amino-benzenesulfonylamino)-phenyl]-furan-2-carbonyl}-amino}-5-guanidino-pentanoic acid | EG00240 (S)-2-[(2-Benzenesulfonylamino-thiophene-3-carbonyl)-amino]-5-guanidino-pentanoic acid |
|---|---|---|
| Structure | 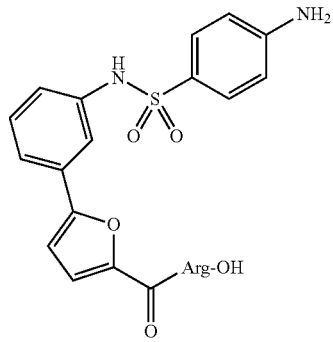 | 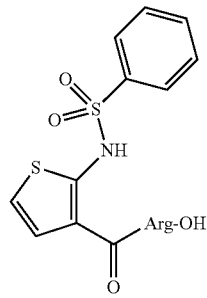 |

| ID | EG00185; (S)-2-{3-[3-(3-Amino-phenyl)-ureido]-benzoylamino}-5-guanidino-pentanoic acid |
|---|---|
| Structure | 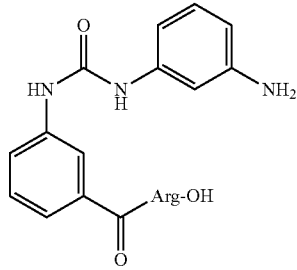 |

| ID | EG00202; (S)-5-Guanidino-2-{[3-(4-nitro-benzenesulfonylamino)-thiophene-2-carbonyl]-amino}-pentanoic acid | EG00203; (S)-2-{[3-(4-Acetylamino-benzenesulfonylamino)-thiophene-2-carbonyl]-amino}-5-guanidino-pentanoic acid |
|---|---|---|
| Structure | 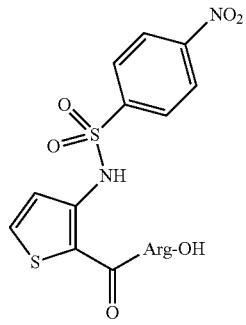 | 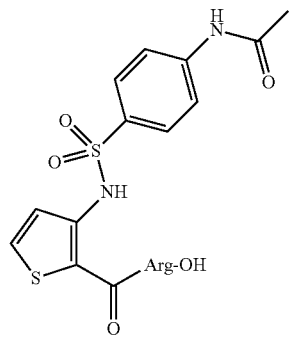 |

| ID | EG00224; (S)-5-Guanidino-2-{[3-(2-nitro-benzenesulfonylamino)-thiophene-2-carbonyl]-amino}-pentanoic acid |
|---|---|
| Structure | 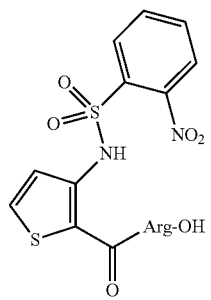 |

TABLE 1-continued

| ID | EG00225; (S)-2-{[3-(2-Amino-benzenesulfonylamino)-thiophene-2-carbonyl]-amino}-5-guanidino-pentanoic acid | EG00226; (S)-2-{[3-(2,4-Difluoro-benzenesulfonylamino)-thiophene-2-carbonyl]-amino}-5-guanidino-pentanoic acid |
|---|---|---|
| Structure | 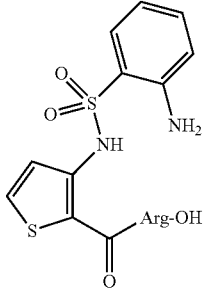 | 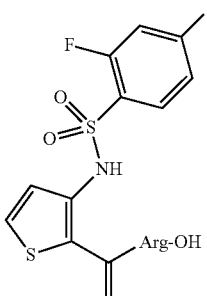 |

| ID | EG00227; (S)-5-Guanidino-2-{[3-(2,4,5-trichloro-benzenesulfonylamino)-thiophene-2-carbonyl]-amino}-pentanoic acid | |
|---|---|---|
| Structure | 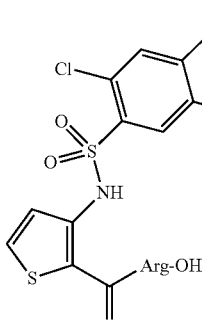 | |

| ID | EG00228; (S)-5-Guanidino-2-{[3-(toluene-4-sulfonylamino)-thiophene-2-carbonyl]-amino}-pentanoic acid | EG00229; (S)-2-{[3-(Benzo[1,2,5]thiadiazole-4-sulfonylamino)-thiophene-2-carbonyl]-amino}-5-guanidino-pentanoic acid |
|---|---|---|
| Structure | 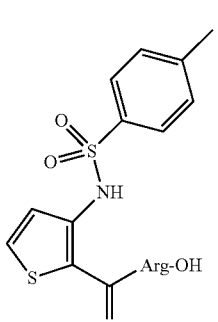 | 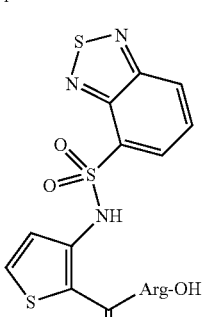 |

| ID | EG00235; (S)-2-{[3-(2,3-Dihydro-benzofuran-5-sulfonylamino)-thiophene-2-carbonyl]-amino}-5-guanidino-pentanoic acid | |
|---|---|---|
| Structure | 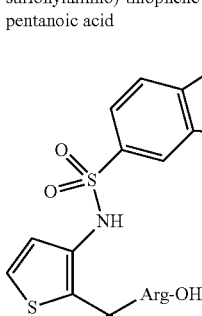 | |

TABLE 1-continued

| ID | EG00260; (S)-5-Guanidino-2-{[3-(2-nitrobenzenesulfonylamino)-5-phenyl-thiophene-2-carbonyl]-amino}-pentanoic acid | EG00263; (S)-2-({3-[3-(4-Aminobutylcarbamoyl)-benzenesulfonylamino]-thiophene-2-carbonyl}-amino)-5-guanidino pentanoic acid |
|---|---|---|
| Structure | | |

| ID | EG00264; (S)-2-{[3-(5-Methyl-benzo[1,2,5]thiadiazole-5-methyl-4-sulfonylamino)-thiophene-2-carbonyl]-amino}-5-guanidino-pentanoic acid |
|---|---|
| Structure | |

| ID | EG00265; (S)-2-{(3-(1,2-Dimethyl-1H-imidazole-4-sulfonylamino)-thiophene-2-carbonyl]-amino}-5-guanidino-pentanoic acid | EG00266; (S)-{[3-(Benzo[1,2,5]thiadiazole-5-sulfonylamino)-thiophene-2-carbonyl]-amino}-5-guanidino-pentanoic acid |
|---|---|---|
| Structure | | |

TABLE 1-continued

| ID | EG00269; (S)-5-Guanidino-2-{[3-(2-nitro-benzenesulfonylamino)-5-(4-nitro-phenyl)-thiophene-2-carbonyl]-amino}-pentanoic acid |

Structure

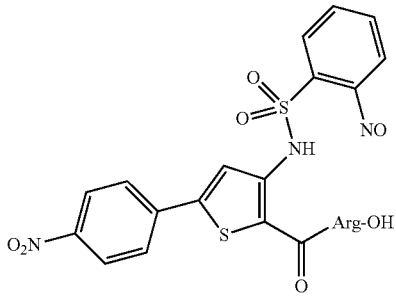

| ID | EG00270; (S)-2-{[3-(4-Bromo-benzenesulfonylamino)-thiophene-2-carbonyl]-amino}-5-guanidino-pentanoic acid | EG00271; (S)-2-{[3-(4-Bromo-2-methoxy-benzenesulfonylamino)-thiophene-2-carbonyl]-amino}-5-guanidino-pentanoic acid |

Structure

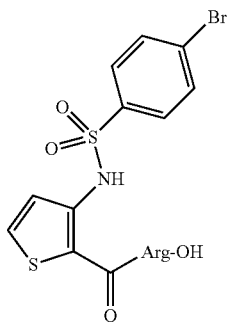 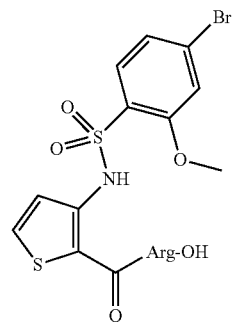

| ID | EG00274; (S)-2-({3-[3-(3-Amino-prop-1-ynyl)-benzenesulfonylamino]-thiophene-2-carbonyl}-amino)-5-guanidino-pentanoic acid |

Structure

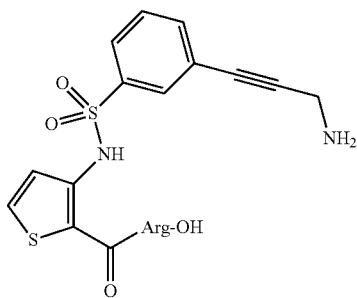

| ID | EG00277; (S)-5-Guanidino-2-{[3-(naphthalene-1-sulfonylamino)-thiophene-2-carbonyl]-amino}-pentanoic acid | EG00278; (S)-2-({3-[3-(2-Amino-ethylcarbamoyl)-benzenesulfonylamino]-thiophene-2-carbonyl}-amino)-5-guanidino-pentanoic acid |

Structure

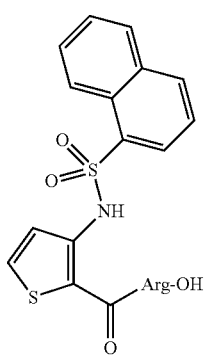 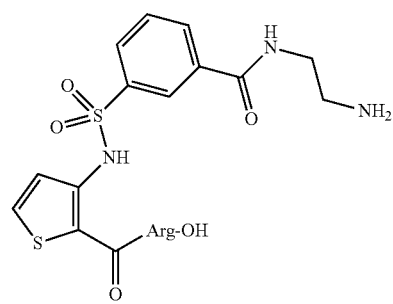

| ID | EG00279; (S)-5-Guanidino-2-({3-[3-(4-[1,2,3]thiadiazol-4-yl-benzylamino)-benzenesulfonylamino]-thiophene-2-carbonyl}-amino)-pentanoic acid |

Structure

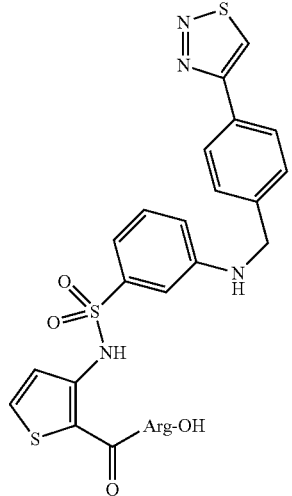

| ID | EG00280; (S)-2-[(3-{3-[(5-Chloro-1,3-dimethyl-1H-pyrazol-4-ylmethyl)-amino]-benzenesulfonylamino}-thiophene-2-carbonyl)-amino]-5-guanidino-pentanoic acid | EG00281; (S)-5-Guanidino-2-({3-[3-(3-methoxy-propylcarbamoyl)-benzenesulfonylamino]-thiophene-2-carbonyl}-amino)-pentanoic acid |

Structure

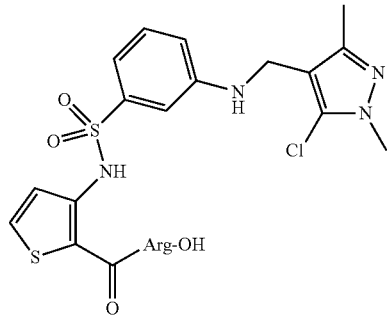 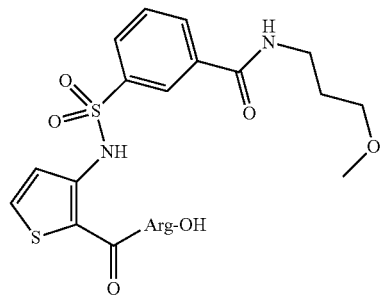

| ID | E000282; (S)-2-({3-[3-(3,4-Dimethoxy-phenylcarbamoyl)-benzenesulfonylamino]-thiophene-2-carbonyl}-amino)-5-guanidino-pentanoic acid |

Structure

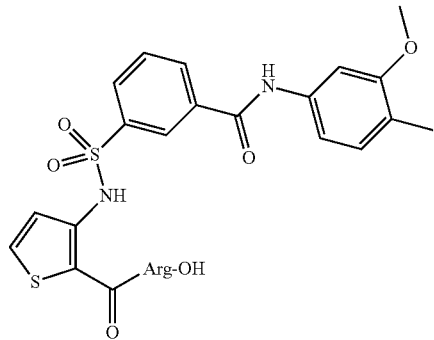

TABLE 1-continued

| ID | EG00283; (S)-5-Guanidino-2-[(3-{3-[(pyridin-2-ylmethyl)-amino]-benzenesulfonylamino}-thiophene-2-carbonyl)-amino]-pentanoic acid | EG00286; (S)-5-Guanidino-2-{[3-(5-pyridin-2-yl-thiophene-2-sulfonylamino)-thiophene-2-carbonyl]-amino}-pentanoic acid |
|---|---|---|
| Structure | 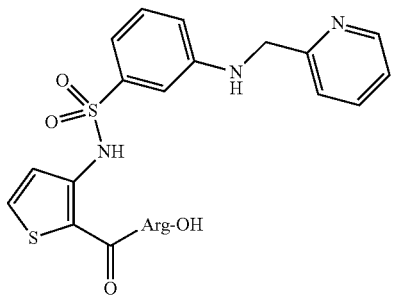 | 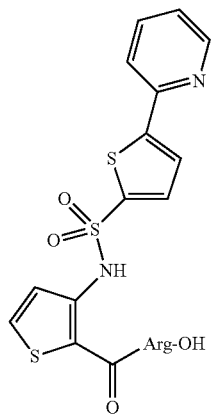 |

| ID | EG00287; (S)-2-{[3-(Benzofuran-2-sulfonylamino)-thiophene-2-carbonyl]-amino}-5-guanidino-pentanoic acid |
|---|---|
| Structure | 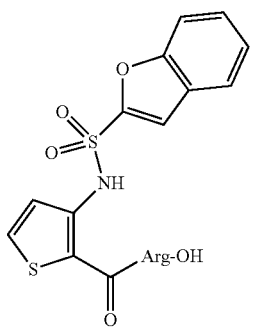 |

| ID | EG00288; (S)-2-{[3-(Benzo[1,2,5]oxadiazole-4-sulfonylamino)-thiophene-2-carbonyl]-amino}-5-guanidino-pentanoic acid | EG00289; (S)-5-Guanidino-2-{[3-(4-methyl-3,4-dihydro-2H-benzo[1,4]oxazine-7-sulfonylamino)-thiophene-2-carbonyl]-amino}-pentanoic acid |
|---|---|---|
| Structure | 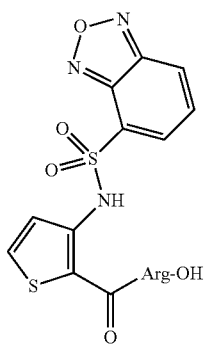 | 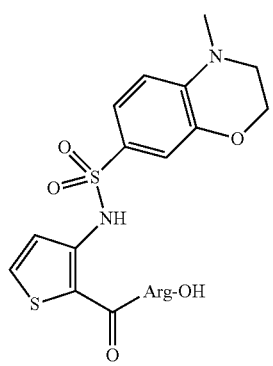 |

| | |
|---|---|
| ID | EG00290; (S)-5-Guanidino-2-{[3-(5-oxazol-5-yl-thiophene-2-sulfonylamino)-thiophene-2-carbonyl]-amino}-pentnoic acid |

Structure

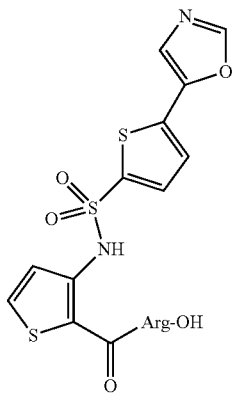

| | | | |
|---|---|---|---|
| ID | EG00291; (S)-2-{[3-(Benzo[b]thiophene-2-sulfonylamino)-thiophene-2-carbonyl]-amino}-5-guanidino-pentanoic acid | | EG00292; (S)-5-Guanidino-2-{[3-(6-phenoxy-pyridine-3-sulfonylamino)-thiophene-2-carbonyl]-amino}-pentanoic acid |

Structure

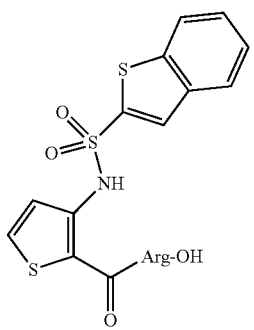    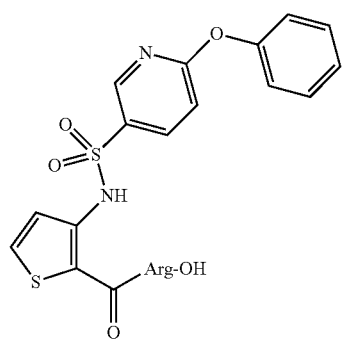

| | |
|---|---|
| ID | E000293; (S)-5-Guanidino-2-({3-[3-(2-methyl-pyrimidin-4-yl)-benzenesulfonylamino]-thiophene-2-carbonyl}-amino)-pentanoic acid |

Structure

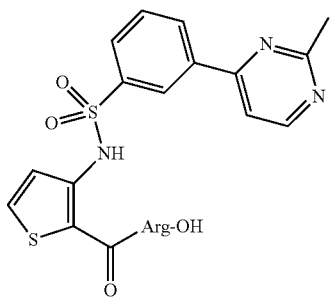

TABLE 1-continued

| ID | EG00294; (S)-5-Guanidino-2-({3-[3-(5-methyl-[1,2,4]oxadiazol-3-yl)-benzenesulfonylamino]-thiophene-2-carbonyl}-amino)-pentanoic acid | E000295; (S)-5-Guanidino-2-{[3-(5-methyl-3-phenyl-isoxazole-4-sulfonylamino)-thiophene-2-carbonyl]-amino}-pentanoic acid |

| ID | EG00296; (S)-2-{[3-(Benzo[1,3]dioxole-5-sulfonylamino)-thiophene-2-carbonyl]-amino}-5-guanidino-pentanoic acid | |

| ID | EG00299; (S)-2-{[3-(5-Bromo-2,3-dihydro-benzofuran-7-sulfonylamino)-thiophene-2-carbonyl]-amino}-5-guanidino-pentanoic acid | EG00301; (S)-5-Guanidino-2-{[3-(3-pyrimidin-5-yl-benzenesulfonylamino)-thiophene-2-carbonyl]-amino}-pentanoic acid |

| ID | EG00303; S)-2-{[3-(2-Cyano-6-methyl-benzenesulfonylamino)-thiophene-2-carbonyl]-amino}-5-guanidino-pentanoic acid |

TABLE 1-continued

| ID | EG00308; (S)-5-Guanidino-2-({3-[3-(3-methyl-3H-imidazol-4-ylethynyl)-benzenesulfonylamino]-thiophene-2-carbonyl}-amino)-pentanoic acid | EG00309; (S)-5-Guanidino-2-({3-[3-(1-methyl-1H-pyrazol-3-ylcarbamoyl)-benzenesulfonylamino]-thiophene-2-carbonyl}-amino)-pentanoic acid |
|---|---|---|
| Structure | 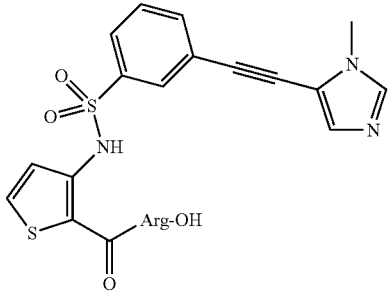 | |

| ID | EG00310; (S)-2-{[3-(3-Furan-2-yl-benzenesulfonylamino)-thiophene-2-carbonyl]-amino}-5-guanidino-pentanoic acid |
|---|---|
| Structure | 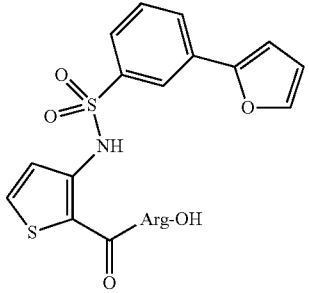 |

| ID | EG00314; (S)-5-Guanidino-2-{[3-(3-thiophen-2-yl-benzenesulfonylamino)-thiophene-2-carbonyl]-amino}-pentanoic acid | EG00316; (S)-2-[(3-{3-[(2,5-Dimethyl-2H-pyrazol-3-ylmethyl)-amino]-benzenesulfonylamino}-thiophene-2-carbonyl)-amino]-5-guanidino-pentanoic acid |
|---|---|---|
| Structure | 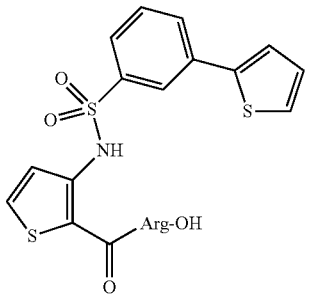 | |

| ID | EG00317; (S)-2-[(3-{3-[(3,5-Dimethyl-isoxazol-4-ylmethyl)-amino]-benzenesulfonylamino}-thiophene-2-carbonyl)-amino]-5-guanidino-pentanoic acid |
|---|---|
| Structure | 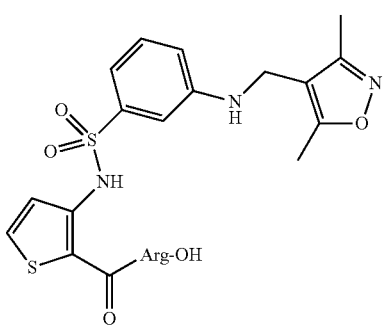 |

TABLE 1-continued

| ID | EG00318; (S)-2-[(3-{3-[(5-Chloro-3-methyl-1-phenyl-1H-pyrazol-4-ylmethyl)-amino]-benzenesulfonylamino}-thiophene-2-carbonyl)-amino]-5-guanidino-pentanoic acid | EG00319; (S)-5-Guanidino-2-[(3-{3-[(1-methyl-1H-indazol-3-ylmethyl)-amino]-benzenesulfonylamino}-thiophene-2-carbonyl)-amino]-pentanoic acid |
|---|---|---|
| Structure | 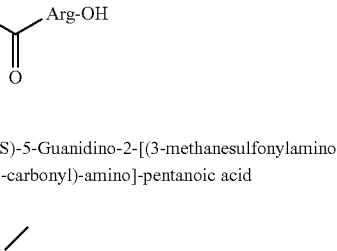 | 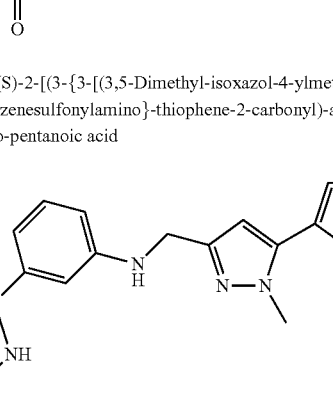 |

| ID | EG00320; (S)-5-Guanidino-2-[(3-methanesulfonylamino-thiophene-2-carbonyl)-amino]-pentanoic acid |
|---|---|
| Structure | 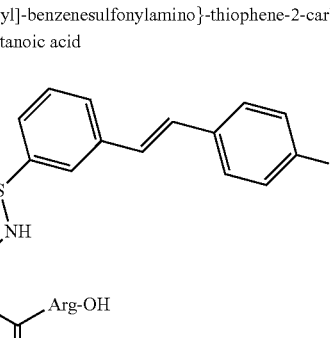 |

| ID | EG00330; (S)-2-[(3-{3-[(3,5-Dimethyl-isoxazol-4-ylmethyl)-amino]-benzenesulfonylamino}-thiophene-2-carbonyl)-amino]-5-guanidino-pentanoic acid | EG00332; (S)-2-[(3-{3-[(2,5-Dimethyl-oxazol-4-ylmethyl)-amino]-benzenesulfonylamino}-thiophene-2-carbonyl)-amino]-5-guanidino-pentanoic acid |
|---|---|---|
| Structure | 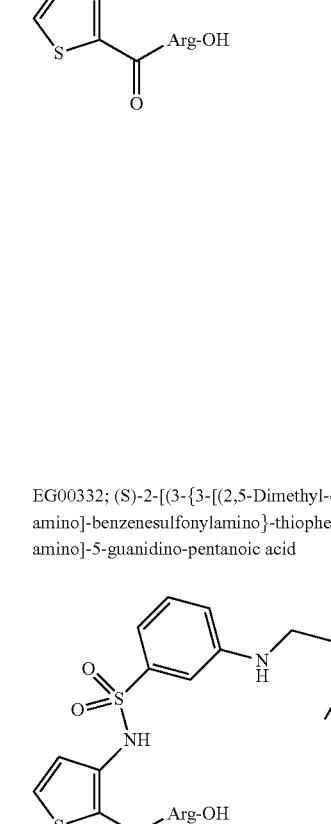 |  |

| ID | EG00337; (S)-5-Guanidino-2-[(3-{3-[(E)-2-(4-methoxy-phenyl)-vinyl]-benzenesulfonylamino}-thiophene-2-carbonyl)-amino]-pentanoic acid |
|---|---|
| Structure |  |

TABLE 1-continued

| ID | EG00338; (S)-5-Guanidino-2-[(3-{3-[2-(4-methoxy-phenyl)-2-oxo-ethyl]-benzenesulfonylamino}-thiophene-2-carbonyl)-amino]-pentanoic acid | EG00340; (S)-2-{[2-(Benzo[1,2,5]thiadiazole-4-sulfonylamino)-4,5-dimethyl-thiophene-3-carbonyl]-amino}-5-guanidino-pentanoic acid |
|---|---|---|
| Structure | 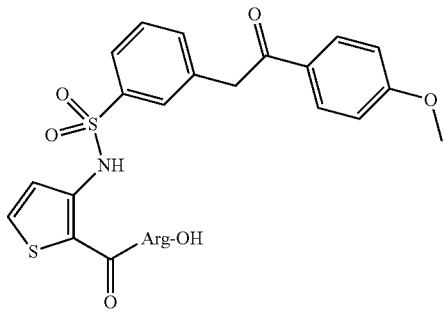 | 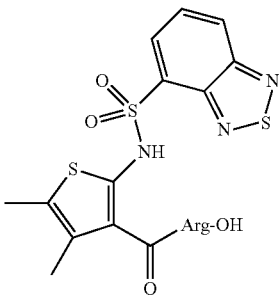 |
| ID | EG00333; (S)-2-[(3-{3-[(1,5-Dimethyl-1H-pyrazol-3-ylmethyl)carbamoyl]benzenesulfonylamino}-thiophene-2-carbonyl)-amino]-5-guanidino-pentanoic acid | |
| Structure | 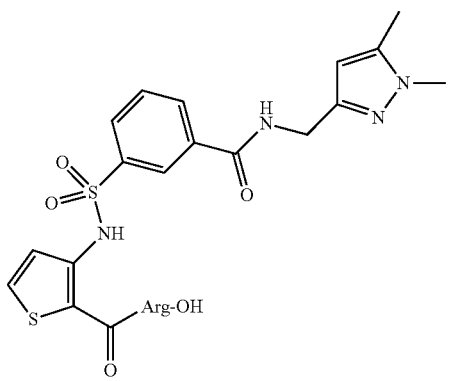 | |
| ID | EG00334; (S)-5-Guanidino-2-[(3-{3-[(1,3,5-trimethyl-1H-pyrazol-4-ylmethyl)-carbamoyl]-benzenesulfonylamino}-thiophene-2-carbonyl)-amino]-pentanoic acid | EG00387; (S)-2-[(3-{4-[(5-Chloro-1,3-dimethyl-1H-pyrazol-4-ylmethyl)-amino]-benzenesulfonyl amino}-thiophene-2-carbonyl)-amino]-5-guanidino-pentanoic acid |
| Structure | 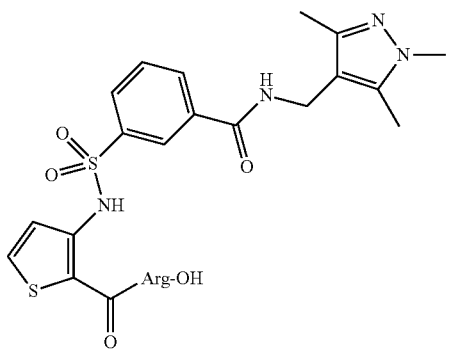 | 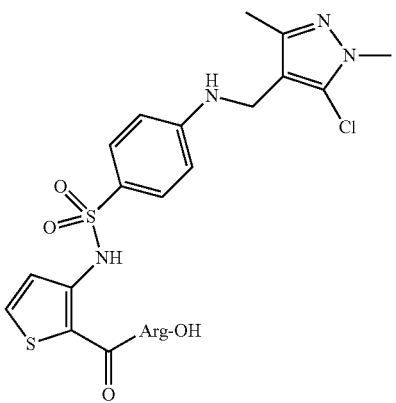 |

TABLE 1-continued

ID    EG00298; (S)-5-Guanidino-2-{[3-(3-pyridin-3-ylethynyl-benzenesulfonylamino)-thiophene-2-carbonyl]-amino}-pentanoic acid Structure

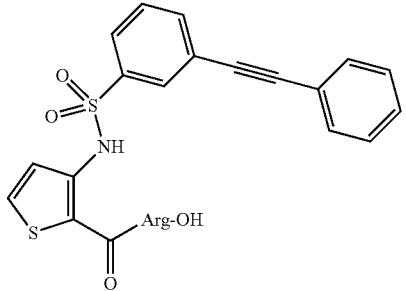

ID    EG00388; (S)-2-[(3-{4-[(2,5-Dimethyl-2H-pyrazol-3-ylmethyl)-amino]-benzenesulfonylamino}-thiophene-2-carbonyl)-amino]-5-guanidino-pentanoic acid    EG00389; (S)-2-[(3-{4-[(3,5-Dimethyl-isoxazol-4-ylmethyl)-amino]-benzenesulfonylamino}-thiophene-2-carbonyl)-amino]-5-guanidino-pentanoic acid Structure

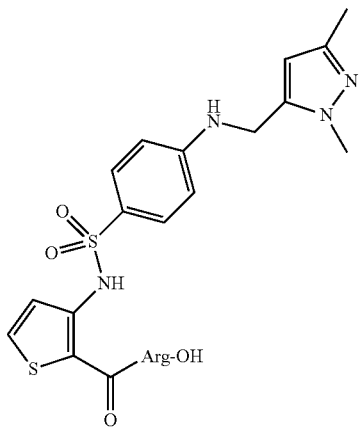 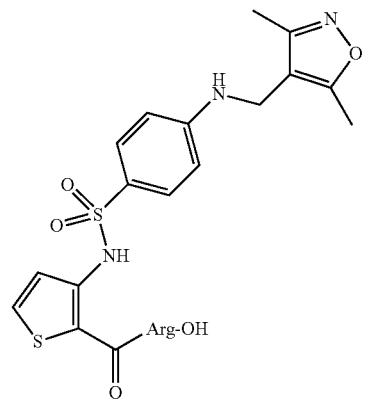

ID    EG00336; (S)-2-[(3-{2-[(5-Chloro-3-methyl-1-phenyl-1H-pyrazol-4-ylmethyl)-amino]-benzenesulfonylamino}-thiophene-2-carbonyl)-amino]-5-guanidino-pentanoic acid Structure

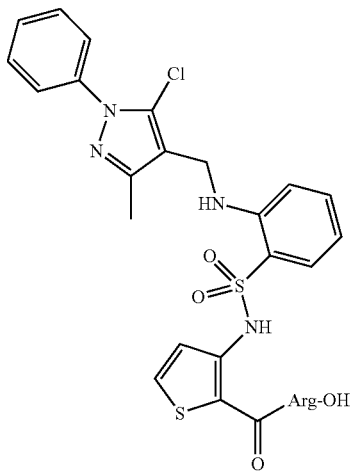

TABLE 1-continued

| ID | EG00413; (S)-2-[(3-{4-[(2,5-Dimethyl-oxazol-4-ylmethyl)-amino]-benzenesulfonylamino}-thiophene-2-carbonyl)-amino]-5-guanidino-pentanoic acid | EG00339; (S)-5-Guanidino-2-[(3-{3-[(5-methyl-isoxazol-3-ylmethyl)-carbamoyl]-benzenesulfonylamino)-thiophene-2-carbonyl)-amino]-pentanoic acid |
|---|---|---|
| Structure | 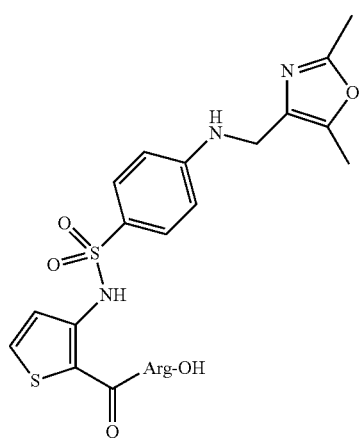 | 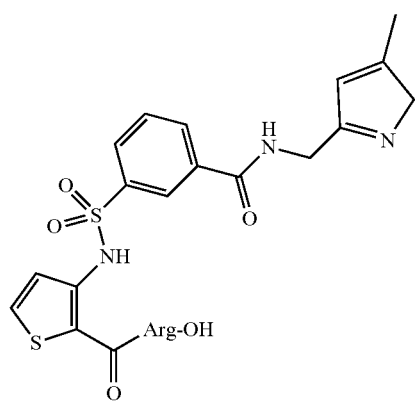 |

| ID | EG00361; (S)-2-[(3-{2-[(4-Chloro-1-methyl-1H-pyrazol-3-ylmethyl)-amino]-benzenesulfonylamino}-thiophene-2-carbonyl)-amino]-5-guanidino-pentanoic acid | |
|---|---|---|
| Structure | 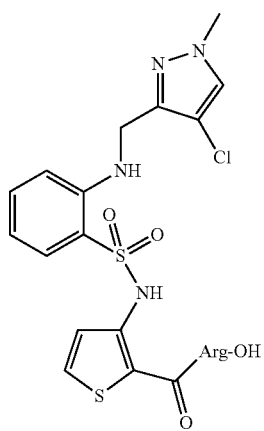 | |

| ID | EG00376; (S)-2-[(3-{2-[(2,5-Dimethyl-oxazol-4-ylmethyl)-amino]-benzenesulfonylamino}-thiophene-2-carbonyl)-amino]-5-guanidino-pentanoic acid | EG00477; (S)-5-Acetimidoylamino-2-[2-(benzo[1,2,5]thiadiazole-4-sulfonylamino)-benzoylamino]-pentanoic acid |
|---|---|---|
| Structure | 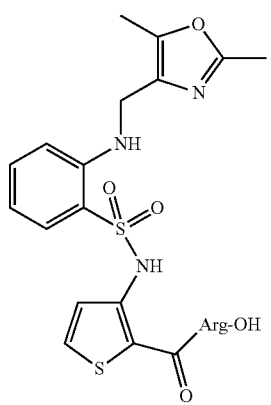 | 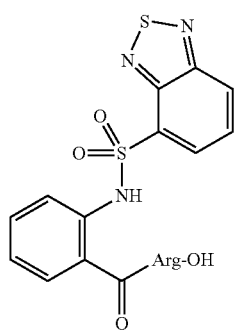 |

TABLE 1-continued

| ID | EG00237; (S)-2-{[5-tert-Butyl-3-(4-methoxy-benzenesulfonylamino)-thiophene-2-carbonyl]-amino}-5-guanidino-pentanoic acid |
|---|---|
| Structure | 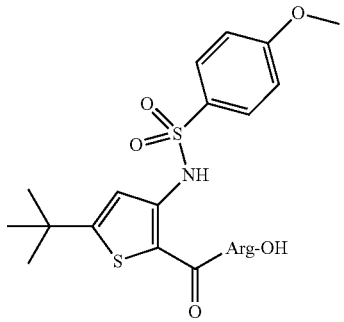 |
| Arg = | 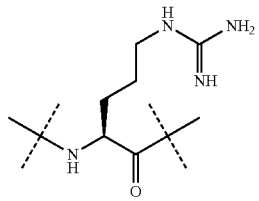 |

Preparation of Alpha-Carbonyl Guanidine Compounds
General Procedure for Solution-Phase PyBroP Coupling

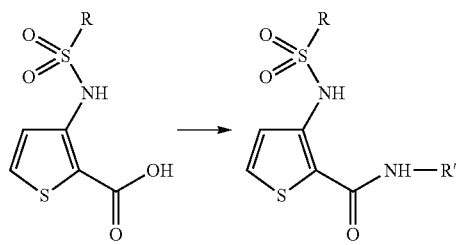

Carboxylic acid (200-300 mg, 1 eq) and bromo-tris-pyrro-lidino-phosphonium hexafluorophosphate (1.1 eq) were suspended in dichloromethane (5 mL) and the mixture was stirred at 20° C. for 10 minutes. N,N-Diisopropylethylamine (7 eq) was added to the mixture and stirred for a further 10 minutes. Suitably-protected amine (derived from aspartic acid, 1.1 eq) was added and the reaction mixture was then stirred for 2 days at 20° C. After this time the reaction solvent was removed in vacuo and the residue partitioned between hydrochloric acid (1M aqueous solution, 20 mL) and ethyl acetate (20 mL). The phases were separated and the aqueous phase extracted with ethyl acetate (3×20 mL). The organic phases were combined and washed with brine (saturated, aqueous solution, 25 mL), dried over magnesium sulfate, filtered and the solvent removed in vacuo to afford the crude residue.

Table 2 summarises the compounds constructed using this method.

TABLE 2

| ID | (S)-2-{[3-(2-Nitro-benzenesulfonylamino)-thiophene-2-carbonyl]-amino-pentanedioic acid 5-tert-butyl ester-1-methyl ester | (S)-2-{[3-(Benzo[1,2,5]thiadiazole-4-sulfonyl amino)-thiophene-2-carbonyl]-amino}-pentanedioic acid 1-tert-butyl ester 5-methyl ester |
|---|---|---|
| Structure | 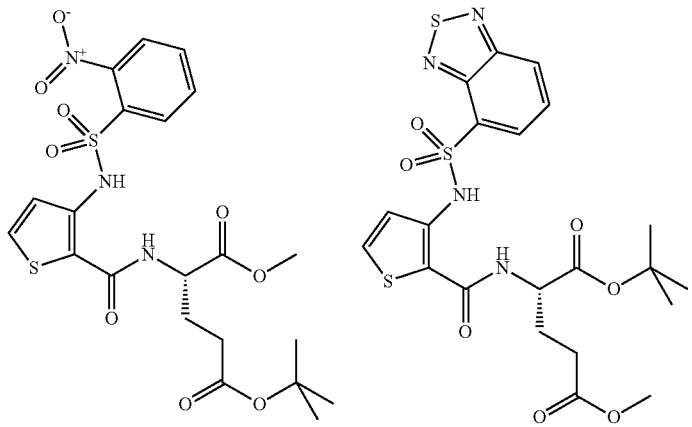 | |

TABLE 2-continued

| ID | (S)-2-{[3-(4-Nitro-benzenesulfonylamino)-thiophene-2-carbonyl]-amino-pentanedioic acid 5-tert-butyl ester-1-methyl ester |
|---|---|
| Structure | 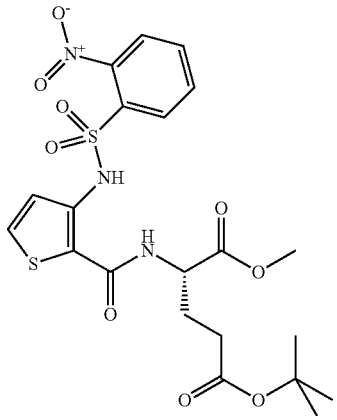 |

General Procedure for Solution-Phase PyBroP Coupling (Side-Chain Acid Coupling)

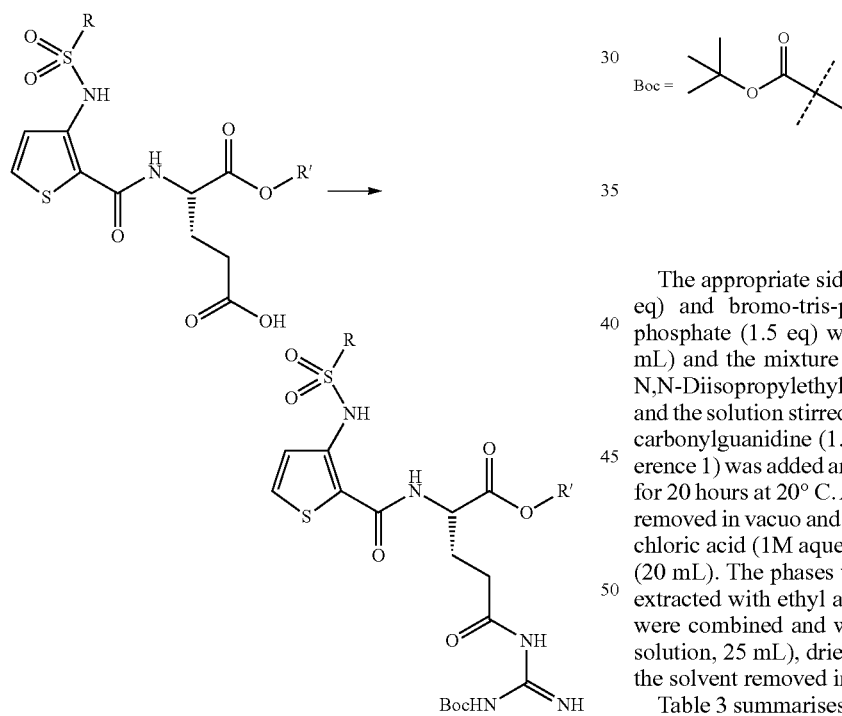

The appropriate side-chain carboxylic acid (50-150 mg, 1 eq) and bromo-tris-pyrrolidino-phosphonium hexafluorophosphate (1.5 eq) were suspended in dichloromethane (5 mL) and the mixture was stirred at 20° C. for 10 minutes. N,N-Diisopropylethylamine (9 eq) was added to the mixture and the solution stirred for a further 10 minutes. Tert-Butoxycarbonylguanidine (1.5 eq, prepared in accordance with reference 1) was added and the reaction mixture was then stirred for 20 hours at 20° C. After this time the reaction solvent was removed in vacuo and the residue partitioned between hydrochloric acid (1M aqueous solution, 20 mL) and ethyl acetate (20 mL). The phases were separated and the aqueous phase extracted with ethyl acetate (3×20 mL). The organic phases were combined and washed with brine (saturated, aqueous solution, 25 mL), dried over magnesium sulfate, filtered and the solvent removed in vacuo to afford the crude residue.

Table 3 summarises the compounds constructed using this method.

TABLE 3

| ID | (S)-2-{[3-(Benzo[1,2,5]thiadiazole-4-sulfonylamino)-thiophene-2-carbonyl]-amino}-5-(tert-butoxycarbonyl)-guanidino-5-oxo-pentanoic acid tert-butyl ester | (S)-5-(tert-butoxycarbonyl)-Guanidino-2-{[3-(4-nitro-enzenesulfonylamino)-thiophene-2-carbonyl]-amino}-5-oxo-pentanoic acid methyl ester |
|---|---|---|

TABLE 3-continued

Structure

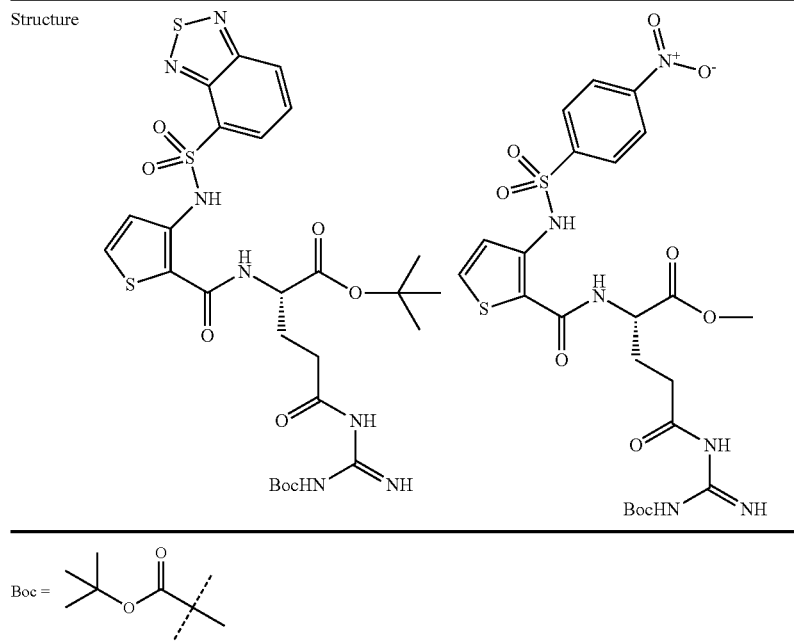

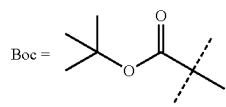

EG00247; (S)-5-guanidino-2-{[3-(4-nitro-benzene-sulfonylamino)-thiophene-2-carbonyl]-amino}-5-oxo-pentanoic acid

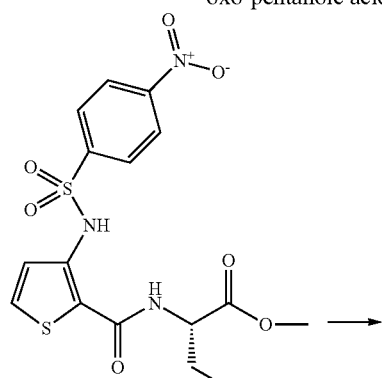

-continued

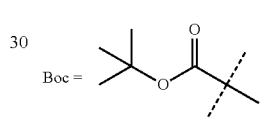

(S)-5-(tert-butoxycarbonyl)-Guanidino-2-{[3-(4-nitro-benzenesulfonylamino)-thiophene-2-carbonyl]-amino}-5-oxo-pentanoic acid methyl ester (10 mg, 0.016 mmol) was stirred with hydrochloric acid (2M aqueous solution:tetrahydrofuran; 1:1) at 80° C. for 4 hours. After this time the reaction solvent was removed in vacuo and the crude residue was purified via elution through a 2 g C-18 column (eluent: water, followed by acetonitrile:water; 20:80) to afford the desired compound, isolated as the hydrochloride salt.

EG00302; (S)-2-{[3-(Benzo[1,2,5]thiadiazole-4-sulfonylamino)-thiophene-2-carbonyl]-amino}-5-guanidino-5-oxo-pentanoic acid

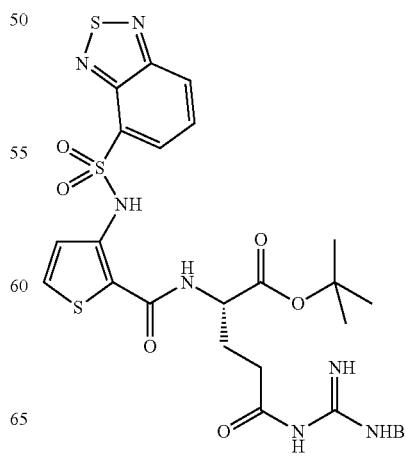

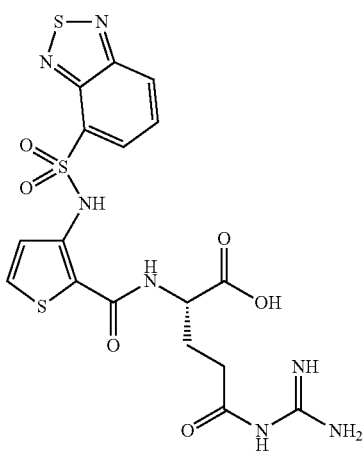

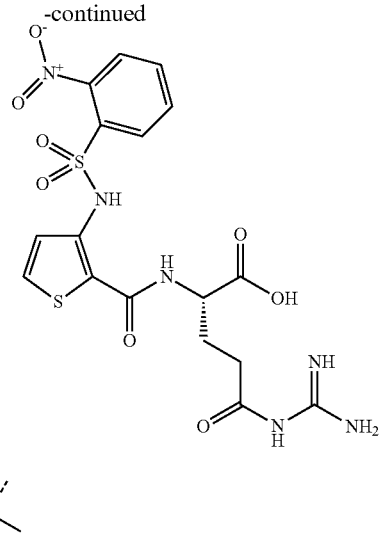

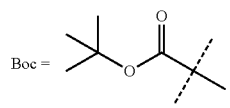

(S)-2-{[3-(Benzo[1,2,5]thiadiazole-4-sulfonylamino)-thiophene-2-carbonyl]-amino}-pentanedioic acid 1-tert-butyl ester 5-methyl ester was stirred in dichloromethane/trifluoroacetic acid (2.5 mL, 5:1) for 16 hours at 20° C. After this time the solvent was removed in vacuo and the resulting yellow residue was purified using preparative LC-MS.

The desired compound was isolated as the trifluoroacetate salt.

EG00285; (S)-5-Guanidino-2-{[3-(2-nitro-benzenesulfonylamino)-thiophene-2-carbonyl]-amino}-5-oxo-pentanoic acid

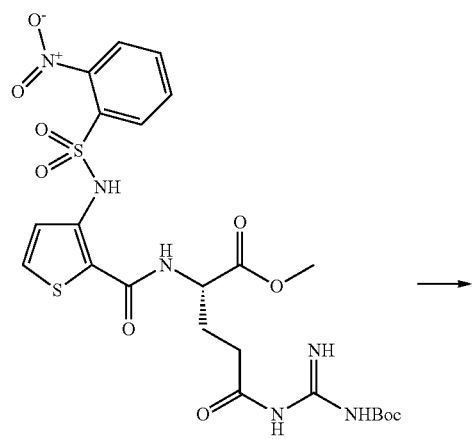

(S)-5-tert-butoxycarbonyl-Guanidino-2-{[3-(2-nitro-benzenesulfonylamino)-thiophene-2-carbonyl]-amino}-5-oxo-pentanoic acid methyl ester was stirred in hydrochloric acid (1:1, 4 M aqueous solution:tetrahydrofuran) at 80° C. for 3 hours, followed by 48 hours at room temperature followed by a further 2 hours at 80° C. The solvent was removed in vacuo and the residue purified by chromatography on a 2 g C-18 column (eluent: water increasing to acetonitrile:water; 20:80) to afford the desired compound, isolated as the hydrochloride salt.

General Procedure for Solution-Phase Suzuki Coupling (Carboxylic Acid Methyl Esters)

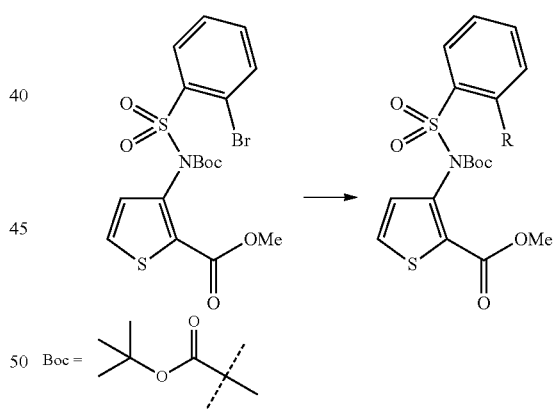

3-(2-Bromo-N-tert-butoxycarbonyl-benzenesulfonylamino)-thiophene-2-carboxylic acid methyl ester (1 eq), the boronic acid (2.5 eq) and potassium phosphate (tribasic, 2 M aqueous solution, 4 eq) were suspended in degassed 1,2-dimethoxyethane (10 mL). The solution was further degassed and [1,1'-bis(diphenylphosphino)ferrocene]dichloropalladium(II) (complex with dichloromethane, 0.1 eq) added in one portion. The reaction mixture was heated at 90° C. for 4 hours. After this time the solvent was removed in vacuo and the brown residue either isolated by one of three methods:

A: Filtration following precipitation with hydrochloric acid (1M, aqueous solution).

B: The residue was partitioned between ethyl acetate and hydrochloric acid (1M aqueous solution). The phases were separated and the aqueous phase extracted with ethyl acetate (3×15 mL), the combined organic extracts were washed with water, brine, dried over magnesium sulfate and the solvent removed in vacuo to afford the desired compounds.

C: Used without any further manipulation.

All were used without further purification in subsequent reactions.

General Procedure for the Hydrolysis of Esters Using Lithium Hydroxide (Preferred Method)

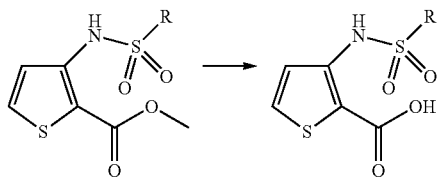

The methyl ester (1 eq) was stirred with lithium hydroxide (2.53 mmol, 3-5 eq) in tetrahydrofuran/methanol/water (10 mL, 5:3:2) at 20 to 80° C. for 3 to 48 hours as necessary. After this time the organic solvent was removed in vacuo, the residue diluted to 5 mL with water and then acidified with hydrochloric acid (1M, aqueous solution, 15 mL) upon which either precipitation occurred and the product was collected by filtration and dried in vacuo; or the aqueous phase was extracted with ethyl acetate (3×10 mL) and the combined organic phases dried over magnesium sulfate and the solvent removed in vacuo to afford the desired products.

General Procedure for Solution-Phase Suzuki Coupling (Carboxylic Acids)

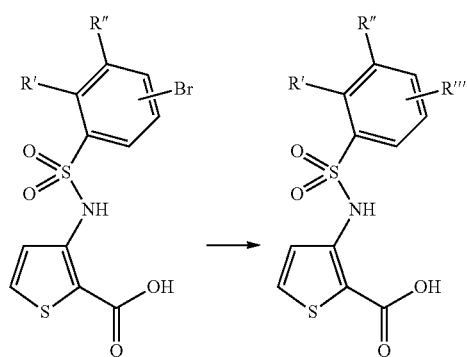

The appropriately substituted 3- and 4-bromophenyl-containing carboxylic acids (50-200 mg, 1 eq), the boronic acid (2.5 eq) and potassium phosphate (tribasic, 2 M aqueous solution, 4 eq) were suspended in degassed 1,2-dimethoxyethane (10 mL). The solution was further degassed and [1,1'-bis(diphenylphosphino)ferrocene]dichloropalladium(II) (complex with dichloromethane, 0.1 eq) added in one portion. The reaction mixture was heated at 90° C. for 4 hours. The reaction mixture was heated at 90° C. for 4 hours. After this time the solvent was removed in vacuo and the brown residue isolated by one of the following methods:

A: Filtration following precipitation with hydrochloric acid (1M, aqueous solution).

B: The residue was partitioned between ethyl acetate and hydrochloric acid (1M aqueous solution). The phases were separated and the aqueous phase extracted with ethyl acetate (3×15 mL), the combined organic extracts were washed with water, brine, dried over magnesium sulfate and the solvent removed in vacuo to afford the desired compounds.

All were used without further purification in subsequent reactions.

General Procedure for PyBroP Coupling in Solution (Using H-Arg(Pbf)-OtBu)

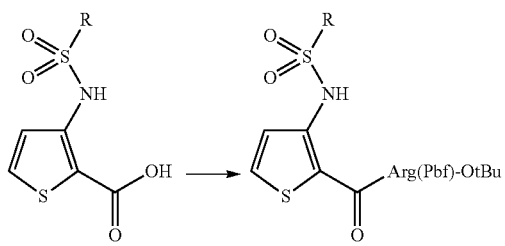

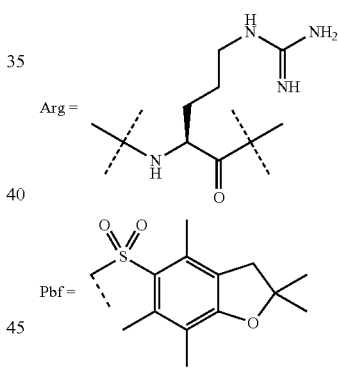

Carboxylic acid (20-100 mg, 1 eq) and bromo-tris-pyrrolidino-phosphonium hexafluorophosphate (1.1 eq) were suspended in dichloromethane (5 mL) and the mixture was stirred at 20° C. for 10 minutes. N,N-Diisopropylethylamine (7.0 eq) was added to the mixture and stirred for a further 10 minutes. Protected amine (1.1 eq) was added and the reaction mixture was then stirred at 20° C. for 16 hours. After this time the solvent was removed in vacuo and the residue partitioned between hydrochloric acid (1M aqueous solution, 20 mL) and ethyl acetate (20 mL). The phases were separated and the aqueous phase extracted with ethyl acetate (3×20 mL). The organic phases were combined and washed with hydrochloric acid (1M aqueous solution, 3×10 mL), brine (saturated, aqueous solution, 25 mL), dried over magnesium sulfate, filtered and the solvent removed in vacuo to afford the desired products as brown residues.

Table 4 summarises the products produced using this method.

TABLE 4

| ID | (S)-5-(2,2,4,6,7-Pentamethyl-2,3-dihydro-benzofuran-5-sulfonyl-guanidino)-2-({3-[4-(1-methyl-1H-pyrazol-4-yl)-benzenesulfonylamino]-thiophene-2-carbonyl}amino)-pentanoic acid tert-butyl ester | (S)-2-({3-[4-(2-Methoxy-pyrimidin-5-yl)-benzenesulfonylamino]-thiophene-2-carbonyl}-amino)-5-(2,2,4,6,7-pentamethyl-2,3-dihydro-benzofuran-5-sulfonyl-guanidino)-pentanoic acid tert-butyl ester |
|---|---|---|
| Structure | 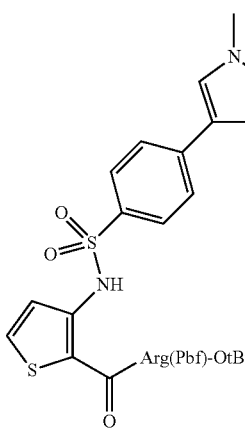 | 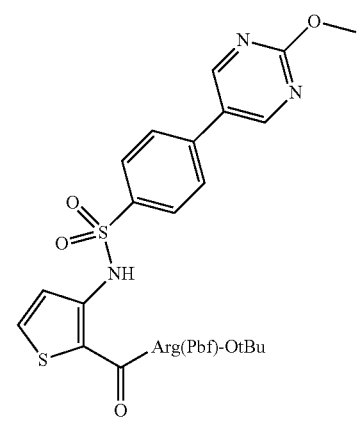 |
| ID | (S)-2-({3-[4-(3,5-Dimethyl-isoxazol-4-yl)-benzenesulfonylamino]-thiophene-2-carbonyl}-amino)-5-(2,2,4,6,7-pentamethyl-2,3-dihydro-benzofuran-5-sulfonyl-guanidino)-pentanoic acid tert-butyl ester | (S)-2-({3-[5-(3,5-Dimethyl-isoxazol-4-yl)-2,3-dihydro-benzofuran-7-sulfonylamino]-thiophene-2-carbonyl}-amino)-5-(2,2,4,6,7-pentamethyl-2,3-dihydro-benzofuran-5-sulfonyl-guanidino)-pentanoic acid tert-butyl ester |
| Structure | 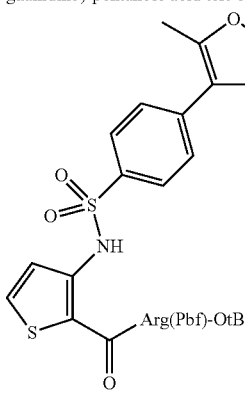 | 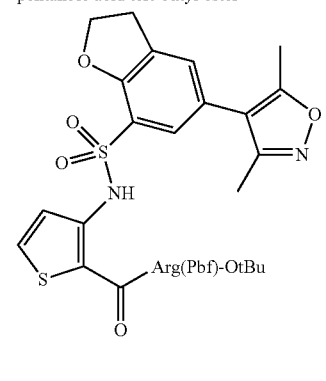 |
| ID | (S)-5-(2,2,4,6,7-Pentamethyl-2,3-dihydro-benzofuran-5-sulfonyl-guanidino)-2-({3-[5-(1-methyl-1H-pyrazol-4-yl)-2,3-dihydro-benzofuran-7-sulfonylamino]-thiophene-2-carbonyl}-amino)-pentanoic acid tert-butyl ester | (S)-5-(2,2,4,6,7-Pentamethyl-2,3-dihydro-benzofuran-5-sulfonyl-guanidino)-2-({3-[5-(4-methyl-3,4-dihydro-2H-pyrido[3,2-b][1,4]oxazin-7-yl)-2,3-dihydro-benzofuran-7-sulfonylamino]-thiophene-2-carbonyl}-amino)-pentanoic acid tert-butyl ester |
| Structure | 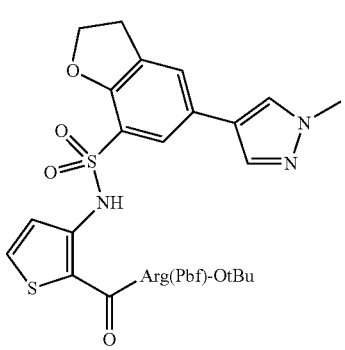 | 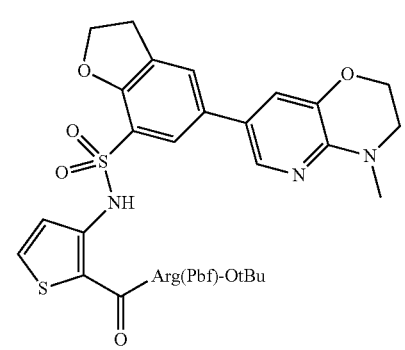 |

TABLE 4-continued

| ID | 2-({3-[3-(4,4,5,5-Tetramethyl-[1,3,2]dioxaborolan-2-yl)-benzenesulfonylamino]-thiophene-2-carbonyl}-amino)-5-(2,2,4,6,7-pentamethyl dihydro-benzofuran-5-sulfonyl-guanidino)-pentanoic acid tert-butyl ester | 2-({3-[3-(Pyridin-4-yl)-benzenesulfonylamino]-thiophene-2-carbonyl}-amino)-5-(2,2,4,6,7-pentamethyldihydro-benzofuran-5-sulfonyl-guanidino)-pentanoic acid tert-butyl ester |
|---|---|---|
| Structure | 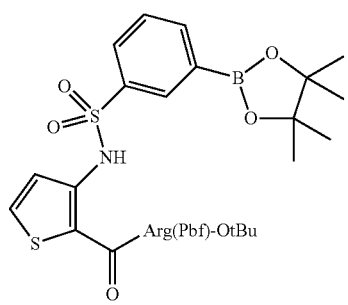 | 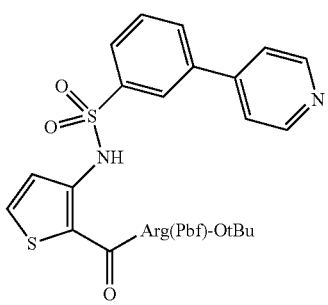 |
| ID | 2-({3-[3-(3,5-Dimethyl-isoxazol-4-yl)-benzene sulfonylamino]-thiophene-2-carbonyl}-amino)-5-(2,2,4,6,7-pentamethyldihydro-benzofuran-5-sulfonyl-guanidino)-pentanoic acid tert-butyl ester | 2-({3-[3-(2,3-Dihydro-benzofuran-5-yl) benzene sulfonylamino}-thiophene-2-carbonyl}-amino)-5-(2,2,4,6,7-pentamethyldihydro-benzofuran-5-sulfonyl-guanidino)-pentanoic acid tert-butyl ester |
| Structure | 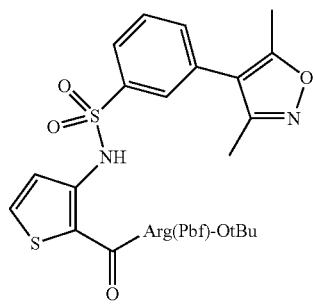 | 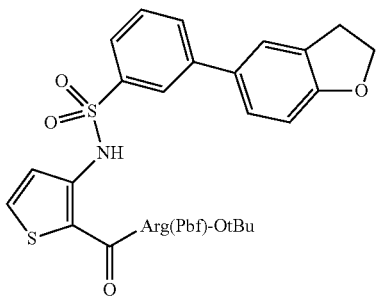 |
| ID | 2-({3-[3-(1-methyl-1H-pyrazol-4-yl)-benzene sulfonylamino]-thiophene-2-carbonyl}-amino)-5-(2,2,4,6,7-pentamethyldihydro-benzofuran-5-sulfonyl-guanidino)-pentanoic acid tert-butyl ester | 2-({3-(3-(2-methoxy-pyrimidin-5-yl))-benzene sulfonylamino]-thiophene-2-carbonyl}-amino)-5-(2,2,4,6,7-pentamethyldihydro-benzofuran-5-sulfonyl-guanidino)-pentanoic acid tert-butyl ester |
| Structure | 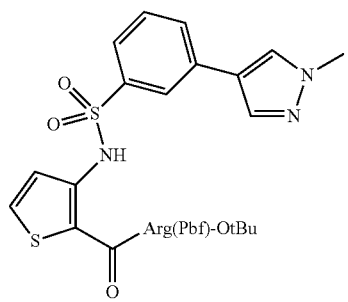 | 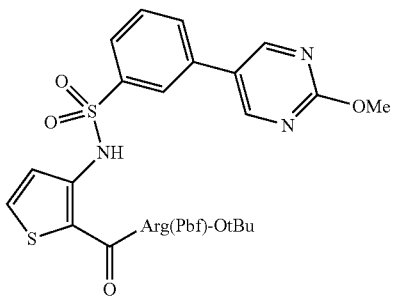 |

TABLE 4-continued

| ID | 2-({3-[2-(pyrimidin-5-yl))-benzene sulfonyl amino]-thiophene-2-carbonyl}-amino)-5-(2,2,4,6,7-pentamethyldihydro-benzofuran-5-sulfonyl-guanidino)-pentanoic acid tert-butyl ester | 2-({3-[2-(1-methyl-1H-pyrazol-4-yl)-benzene sulfonylamino]-thiophene-2-carbonyl}-amino)-5-(2,2,4,6,7-pentamethyldihydro-benzofuran-5-sulfonyl-guanidino)-pentanoic acid tert-butyl ester |
|---|---|---|
| Structure | 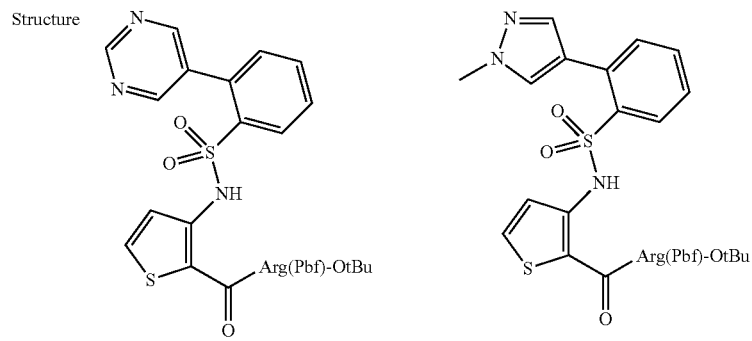 | |
| ID | 2-({3-[2-(3,5-Dimethyl-isoxazol-4-yl)-benzenesulfonylamino]-thiophene-2-carbonyl}-amino)-5-(2,2,4,6,7-pentamethyldihydro-benzofuran-5-sulfonyl-guanidino)-pentanoic acid tert-butyl ester | 2-({3-[2-(2,3-dihydro-benzofuran-5-yl) benzenesulfonylamino]-thiophene-2-carbonyl}-amino)-5-(2,2,4,6,7-pentamethyldihydro-benzofuran-5-sulfonyl-guanidino)-pentanoic acid tert-butyl ester |
| Structure | 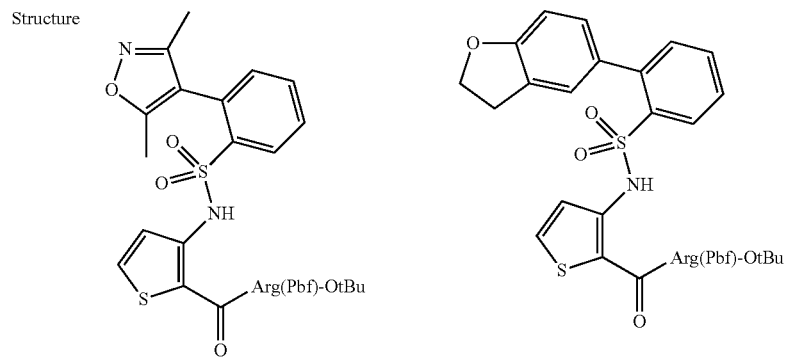 | |
| ID | 2-({3-[2-(2-methoxy-pyrimidin-5-yl))-benzenesulfonylamino]-thiophene-2-carbonyl}-amino)-5-(2,2,4,6,7-pentamethyldihydro-benzofuran-5-sulfonyl-guanidino)-pentanoic acid tert-butyl ester | 2-({3-[2-(pyridin-4-yl)-benzenesulfonyl amino]-thiophene-2-carbonyl}-amino)-5-(2,2,4,6,7-pentamethyldihydro-benzofuran-5-sulfonyl-guanidino)-pentanoic acid tert-butyl ester |
| Structure | 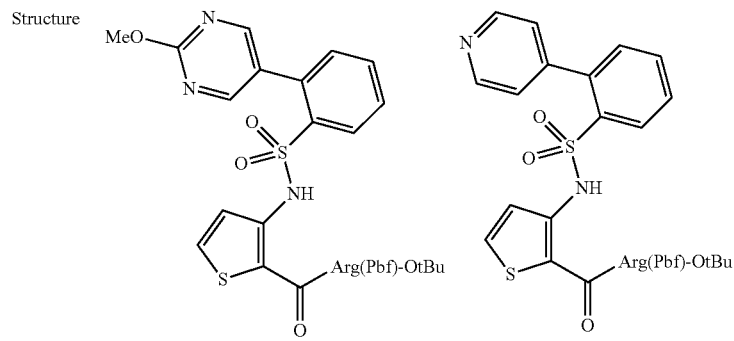 | |

TABLE 4-continued

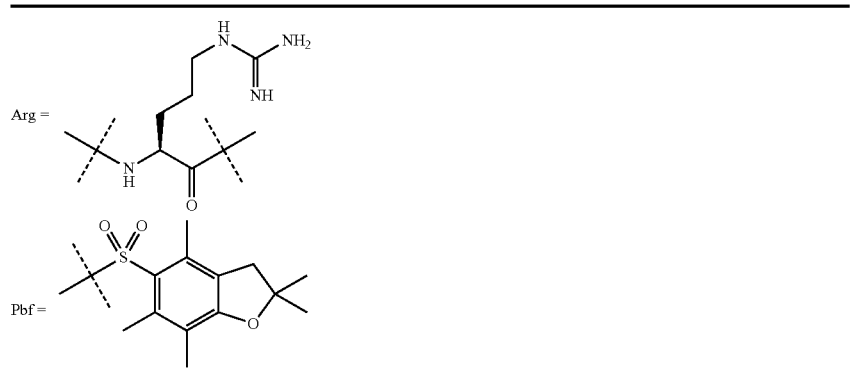

EG00400/(S)-2-{[3-(3-Boronoxy-benzenesulfonylamino)-thiophene-2-carbonyl]-amino}-5-guanidinopentanoic aid

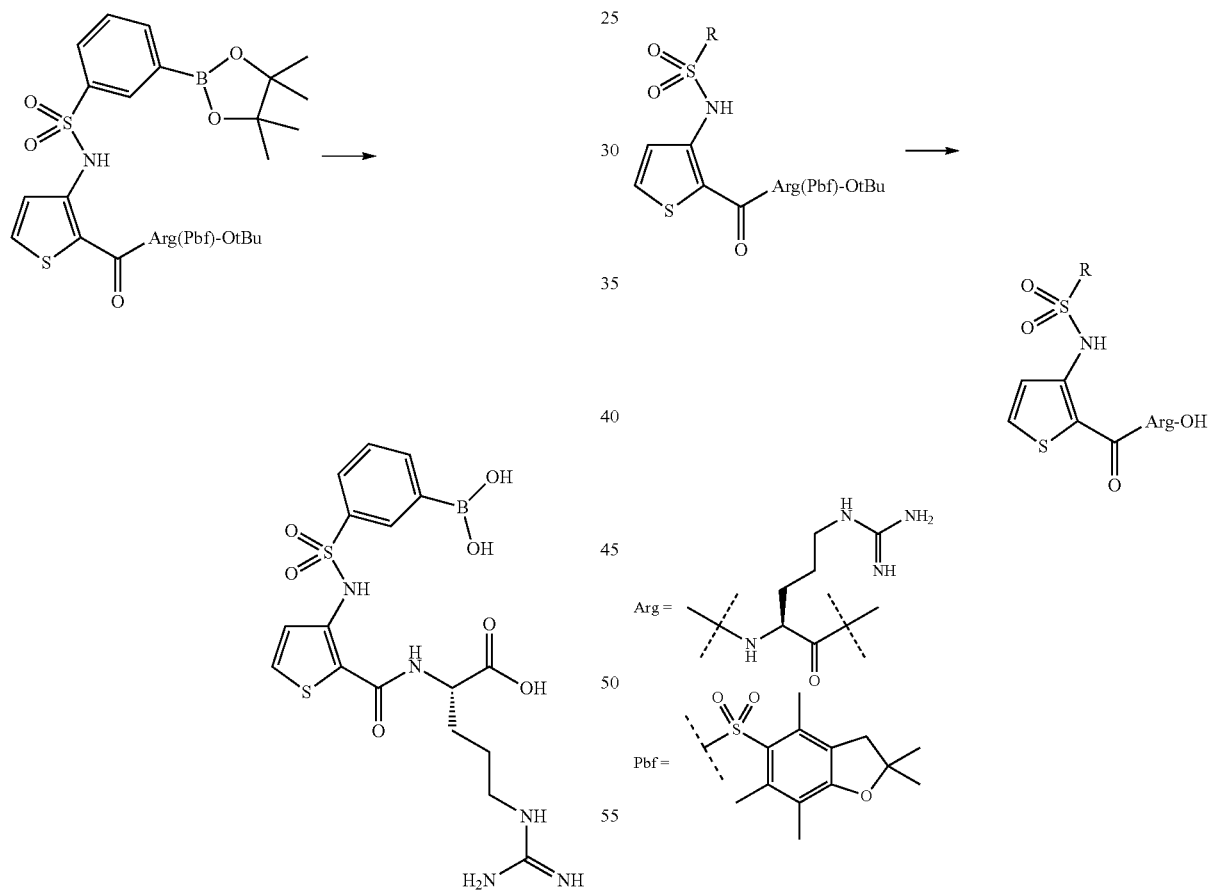

The pinacol, tert-butoxy and 2,2,4,6,7-pentamethyldihydrobenzofuran-5-sulfonyl protected compound was dissolved in trifluoroacetic acid/triisopropylsilane/water (10 mL, 95:2.5:2.5), the reaction mixture was stirred at 20° C. for 2 days. The solvents were removed in vacuo and the resulting yellow residue was purified using preparative LC-MS.

The desired compound was isolated as the trifluoroacetate salt.

General Procedure for the Removal of Tert-Butyl and 2,2,4,6,7-pentamethyldihydrobenzofuran-5-sulfonyl Groups Using Trifluoroacetic Acid The tert-butoxy and 2,2,4,6,7-pentamethyldihydrobenzofuran-5-sulfonyl protected compounds were dissolved in trifluoroacetic acid/triisopropylsilane/water (10 mL, 95:2.5:2.5) and the reaction mixture was stirred at 20° C. for 2 days. The solvents were removed in vacuo and the compound were purified using preparative LC-MS.

All final compounds were isolated as trifluoroacetate salts.

Table 5 summarises the final compounds constructed using these methods.

TABLE 5

| ID | EG00401; (S)-5-Guanidino-2-{[3-(3-pyridin-4-yl-benzenesulfonylamino)-thiophene-2-carbonyl]-amino}-pentanoic acid | EG00324; (S)-5-Guanidino-2-{[3-(2-pyridin-4-yl-benzenesulfonylamino)-thiophene-2-carbonyl]-amino}-pentanoic acid |
|---|---|---|
| Structure | 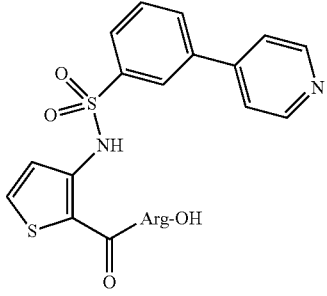 | |

| ID | EG00425; (S)-5-Guanidino-2-({3-[4-(1-methyl-1H-pyrazol-4-yl)-benzenesulfonylamino]-thiophene-2-carbonyl}-amino)-pentanoic acid | EG00426; (S)-5-Guanidino-2-({3-[4-(2-methoxy-pyrimidin-5-yl)-benzenesulfonylamino]-thiophene-2-carbonyl}-amino)-pentanoic acid |
|---|---|---|
| Structure | 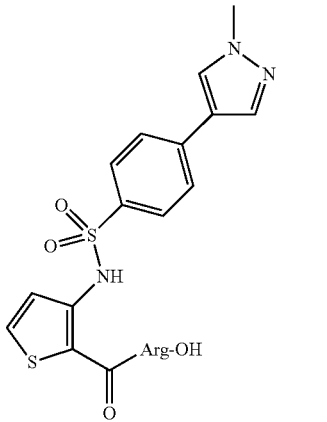 | |

| ID | EG00427; (S)-2-({3-[4-(3,5-Dimethyl-isoxazol-4-yl)-benzenesulfonylamino]-thiophene-2-carbonyl}-amino)-5-guanidino-pentanoic acid | EG00428; (S)-2-({3-[5-(3,5-Dimethyl-isoxazol-4-yl)-2,3-dihydro-benzofuran-7-sulfonyl amino]-thiophene-2-carbonyl}-amino)-5-guanidino-pentanoic acid |
|---|---|---|
| Structure | 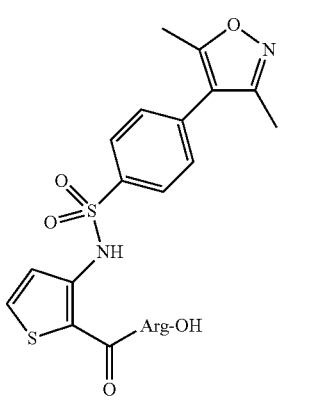 | |

TABLE 5-continued

| ID | EG00429; (S)-5-Guanidino-2-({3-[5-(1-methyl-1H-pyrazol-4-yl)-2,3-dihydro-benzofuran-7-sulfonylamino]-thiophene-2-carbonyl}-amino)-pentanoic acid | EG00343; (S)-2-({3-[2-(3,5-Dimethyl-isoxazol-4-yl)-benzenesulfonylamino]-thiophene-2-carbonyl}-amino)-5-guanidino-pentanoic acid |
|---|---|---|
| Structure | | |

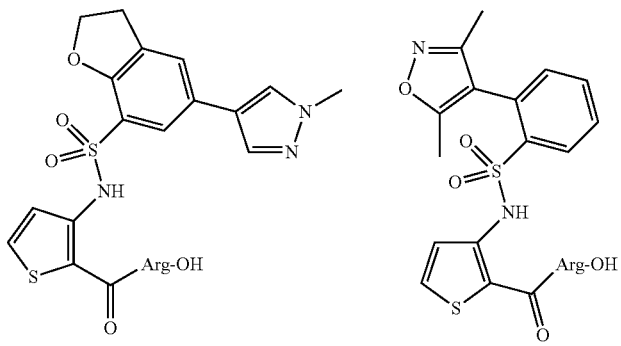

| ID | EG00345; (S)-5-Guanidino-2-({3-[2-(1-methyl-1H-pyrazol-4-yl)-benzenesulfonylamino]-thiophene-2-carbonyl}-amino)-pentanoic acid | EG00346; (S)-5-Guanidino-2-{[3-(2-pyrimidin-5-yl-benzenesulfonylamino)-thiophene-2-carbonyl]-amino}-pentanoic acid |
|---|---|---|
| Structure | | |

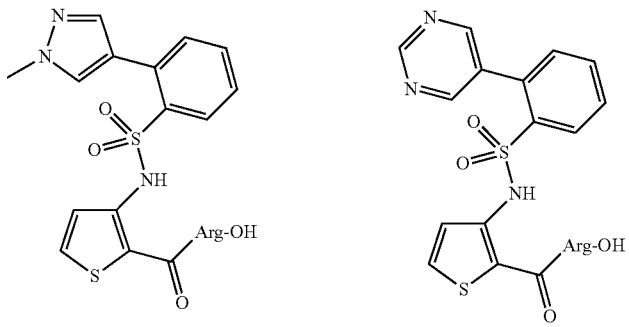

| ID | EG00347; (S)-5-Guanidino-2-({3-[3-(2-methoxy-pyrimidin-5-yl)-benzenesulfonylamino]-thiophene-2-carbonyl}-amino)-pentanoic acid | EG00349; (S)-5-Guanidino-2-({3-[3-(1-methyl-1H-pyrazol-4-yl)-benzenesulfonylamino]-thiophene-2-carbonyl}-amino)-pentanoic acid |
|---|---|---|
| Structure | | |

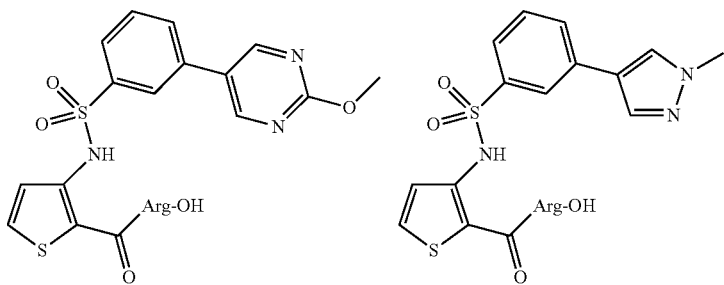

TABLE 5-continued

| ID | EG00350; (S)-2-({3-[3-(3,5-Dimethyl-isoxazol-4-yl)-benzenesulfonylamino]-thiophene-2-carbonyl}-amino)-5-guanidino-pentanoic acid | EG00475; (S)-5-Guanidino-2-({3-[5-(4-methyl-3,4-dihydro-2H-pyrido[3,2-b][1,4]oxazin-7-yl)-2,3-dihydro-benzofuran-7-sulfonylamino]-thiophene-2-carbonyl}-amino)-pentanoic acid |
|---|---|---|
| Structure | 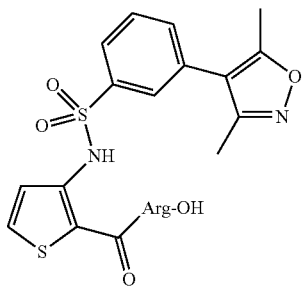 | 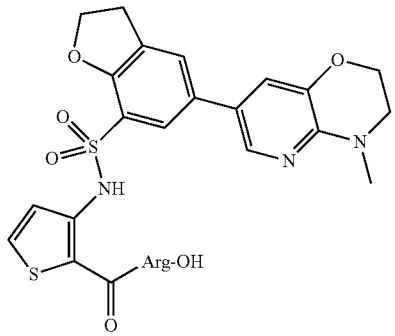 |

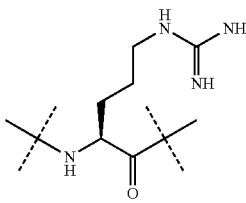

Arg =

EG00323; (S)-5-Guanidino-2-({3-[3-(2-pyridin-3-yl-ethyl)-benzenesulfonylamino]-thiophene-2-carbonyl}-amino)-pentanoic aid

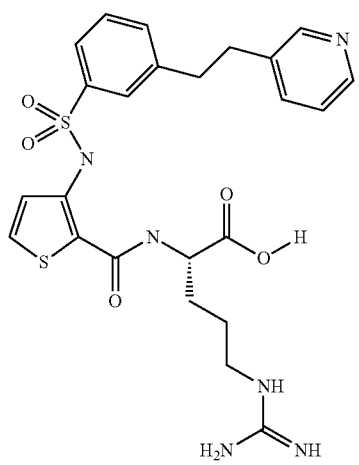

EG00369; (S)-2-({3-[3-(3-Amino-propyl)-benzenesulfonylamino]-thiophene-2-carbonyl}-amino)-5-guanidino-pentanoic acid

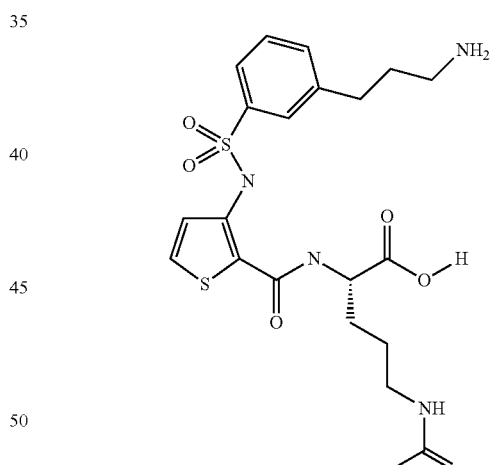

The acetylene (EG00298/5-Guanidino-2-{[3-(3-pyridin-3-ylethynyl-benzenesulfonyl amino)-thiophene-2-carbonyl]amino}-pentanoic acid; approx 10 mg) was dissolved in tetrahydrofuran:water (4:1, 2 mL), palladium on charcoal (approx 10% weight) was added and a hydrogen atmosphere introduced by balloon. The reaction mixture was stirred at 20° C. for 24 hours with occasional refilling of the hydrogen balloon. After this time the reaction mixture was filtered over Celite™ and the solvent removed in vacuo. The yellow residue was purified using preparative LCMS.

The acetylene (EG00274/(S)-2-({3-[3-(3-Amino-prop-1-ynyl)-benzenesulfonylamino]-thiophene-2-carbonyl}-amino)-5-guanidino-pentanoic acid; approx 10 mg) was dissolved in tetrahydrofuran:water (4:1, 2 mL), palladium on charcoal (approx 10% weight) was added and a hydrogen atmosphere introduced by balloon. The reaction mixture was stirred at 20° C. for 24 hours with occasional refilling of the hydrogen balloon. After this time the reaction mixture was filtered over Celite™ and the solvent removed in vacuo. The yellow residue was purified using preparative LCMS and the desired compound isolated as the trifluoroacetate salt.

EG00466, 3-(Benzo[1,2,5]thiadiazole-4-sulfonylamino)-thiophene-2-carboxylic acid ((S)-4-guanidino-1-hydroxycarbamoyl-butyl)-amide

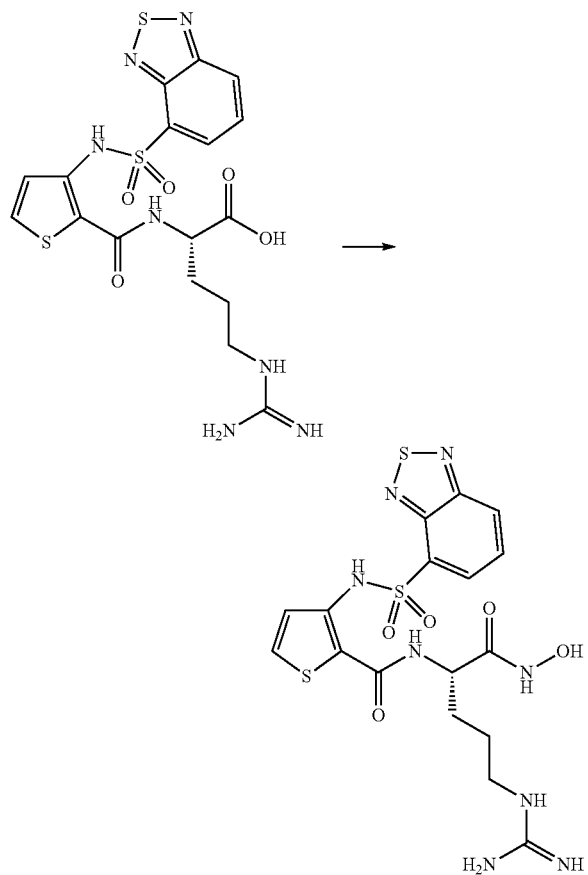

EG00229/(S)-2-{[3-(Benzo[1,2,5]thiadiazole-4-sulfonylamino)-thiophene-2-carbonyl]-amino}-5-guanidino-pentanoic acid (1.0 eq), N,N-diisopropylethylamine (9.0 eq) and HATU (2-(7-aza-1H-benzotriazole-1-yl)-1,1,3,3-tetramethyluronium hexafluorophosphate, 1.5 eq) were stirred in N,N-dimethylformamide (2 mL) at 40° C. for 30 minutes. Hydroxylamine hydrochloride (1.5 eq) was added and the reaction mixture stirred at 40° C. for 16 hours. After this time the solvent was removed in vacuo and the yellow residue was purified using preparative LCMS. The desired compound was isolated as the trifluoroacetate salt.

Described below are experimental methods for various binding and adhesion studies, which were carried out on several compounds of the invention. Results of these studies are given below.

General Experimental Methods

Cell Culture

Porcine aortic endothelial cells expressing neuropilin-1 (PAE/NP-1) were cultured in Ham's F12 medium containing 10% fetal bovine serum (FBS) and 25 µg/ml hygromycin B. PAE cells expressing KDR (PAE/KDR) were grown in Ham's F12 medium containing 10% FBS and 250 µg/ml Gentamicin G418. Human carcinoma cell lines (DU145, A549 and ACHN) were grown in RPMI 1640 medium containing 10% FBS and L-glutamine.

$^{125}$I-VEGF-A$_{165}$ Binding

Confluent cells in 24-well plates were washed twice with phosphate-buffered saline (PBS). At 4° C. various concentrations of peptides or peptidomimetics diluted in binding medium (Dulbecco's modified Eagle's medium, 25 mM HEPES pH 7.3 containing 0.1% BSA) were added, followed by addition of 0.1 nM of $^{125}$I-VEGF-A$_{165}$ (1200-1800 Ci/mmol, GE Healthcare). After 2 h of incubation at 4° C., the medium was aspirated and washed 4 times with cold PBS. The cells were lysed with 0.25 M NaOH, 0.5% SDS solution, and the bound radioactivity of the lysates was measured in a γ counter. Non-specific binding was determined in the presence of 100-fold excess unlabelled VEGF-A$_{165}$.

Cell-Matrix Adhesion

Cell adhesion to extracellular matrix proteins (basement membrane protein complex, laminin I, collagen IV, fibronectin or vitronectin) was measured by the Innocyte ECM cell adhesion assay (Calbiochem). Cells were detached with a non-enzyme cell dissociation solution (Sigma), washed and resuspended in RPMI 1640 medium. Cells with or without peptidomimetic treatment were seeded at 3×10$^4$ cells per matrix-coated well of 96-well plates. After 1.5 h incubation, cells were washed with PBS. The attached cells were labelled with the green fluorescent dye calcein-AM and measured using a fluorescence plate reader at an excitation wavelength of 485 nm and an emission wavelength of 520 nm.

Cell Migration

Cell migration was measured in chemotaxis 24-transwell plates with collagen I-coated inserts. The various concentrations of serum in RPMI 1640/0.1% BSA were placed in the bottom wells of the plates, while top inserts incorporating PET (polyethylene terephthalate) track-etched membranes with 8 micron pores (Becton Dickinson Biosciences) were placed over the bottom wells. Cells were trypsinised, washed and resuspended in RPMI 1640/0.1% BSA. 1.5×10$^6$ cells with or without peptide or peptidomimetic treatment as indicated were loaded into each top inserts, and the chemotaxis trans-well plates were incubated at 37° C. for 4 h. After the incubation, non-migrated cells on the top side of the transwell membranes were removed, and migrated cells on the under side of the trans-well membranes were stained with the REASTAIN Quick-Diff kit (REAGENA). The stained cells from each well were counted in 4 fields at ×100 magnification using an eyepiece indexed graticule (100 grids).

Cell Viability

Cell viability was determined by measurement of conversion of the tetrazolium salt XTT to form formazon dye. Carcinoma cells were seeded at a density of 4×10$^3$ cells per well in 96-well plates in the absence or presence of NP-1 peptide or peptidomimetic antagonists. After 44 h incubation, XTT labelling reagent mixture (Roche) was added to the cultures and they were incubated for a further 4 h. The formazon production was then measured at A$_{490}$ nm with a reference wavelength at 595 nm.

Results

In the cell-matrix adhesion studies, it was found that EG00144 was effective, at concentrations from 10-100 µM, at inhibiting the adhesion of DU145 cancer cells to extracellular matrix proteins.

In the cell migration studies, it was found that EG00144 decreased migration of A549 and ACHN cells, at concentrations from 10-100 µM.

In the cell viability studies, it was found that EG00229 reduced the viability of A549 cells, at a concentration of 100 µM.

The following compounds have an IC$_{50}$ of less than 20 µM: EG00144, EG00174, EG00203, EG00224, EG00225, EG00229, EG00264, EG00265, EG00274, EG00280, EG00283, EG00285, EG00287, EG00288, EG00291, EG00299, EG00316, EG00317, EG00318, EG00319, EG00323, EG00332, EG00350, EG00369, EG00428, EG00475.

The invention claimed is:

1. A compound of the formula

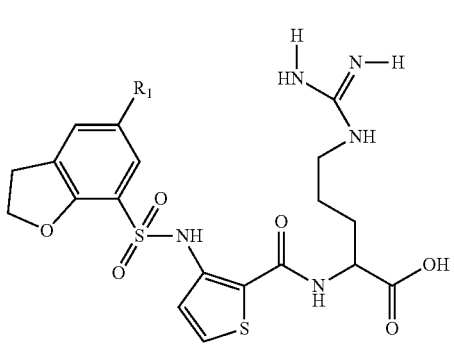

wherein R1 is selected from the group consisting of: NH2; (2-(piperazin-1-yl)thiazol-4-yl)methanamine, N,N-dimethylthiazol-2-amine; and a phenylmethanamine of the following structure:

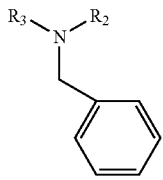

wherein R2 and R3 are each independently selected from H, heterocyclic, and methylisoxazole.

2. A compound of claim 1 comprising 2-{[3-(5-Amino-2,3-dihydro-benzofuran-7-sulfonylamino)-thiophene-2-carbonyl]-amino}-5-guanidino-pentanoic acid

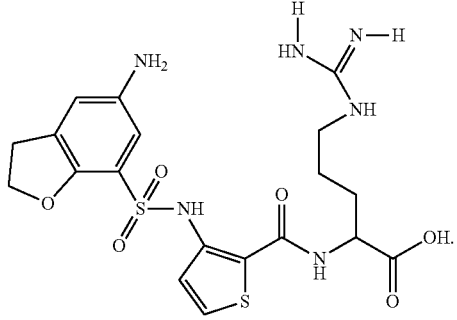

3. A compound of claim 1 comprising 5-Guanidino-2-[(3-{5-[(2-piperazin-1-yl-thiazol-4-ylmethyl)-amino]-2,3-dihydro-benzofuran-7-sulfonylamino}-thiophene-2-carbonyl)-amino]-pentanoic acid

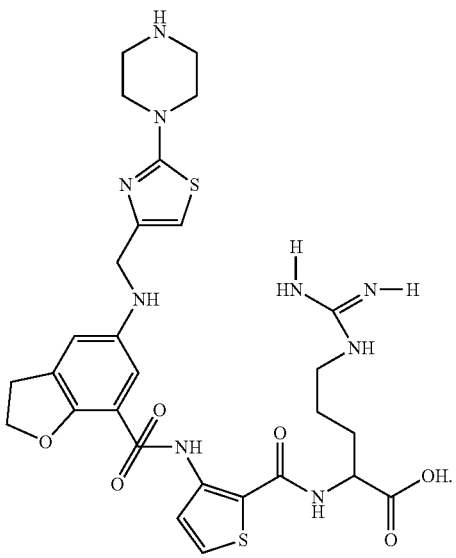

4. A compound of claim 1 comprising 2-({3-[5-(2-Dimethylamino-thiazol-4-yl)-2,3-dihydro-benzofuran-7-sulfonylamino]-thiophene-2-carbonyl}-amino)-5-guanidino-pentanoic acid

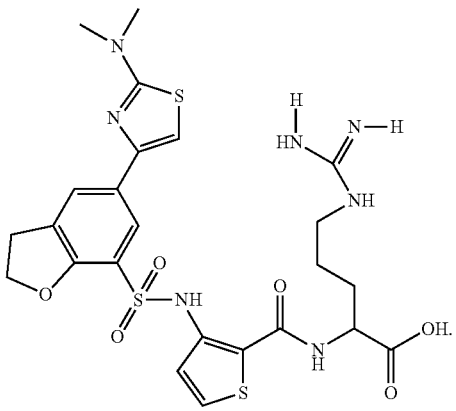

5. A compound of claim 1, wherein R1 is a phenylmethanamine

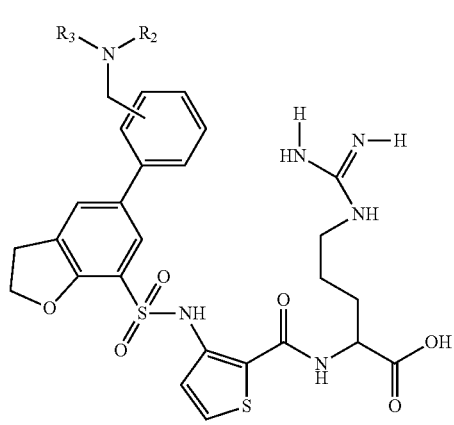

(Ib)

And wherein R2 and R3 are each independently selected from H, heterocyclic, and methylisoxazole.

6. A compound of claim 5 comprising 2-(3-(5-(4-(aminomethyl)phenyl)-2,3-dihydrobenzofuran-7-sulfonamido)thiophene-2-carboxamido)-5-guanidinopentanoic acid

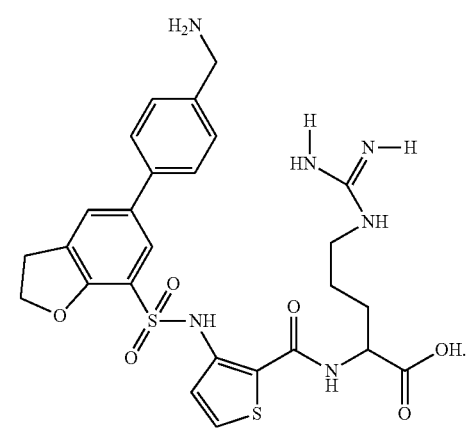

7. A compound of claim 5 comprising 5-guanidino-2-(3-(5-(3-(((5-methylisoxazol-3-yl)methylamino)methyl)phenyl)-2,3-dihydrobenzofuran-7-sulfonamido)thiophene-2-carboxamido)pentanoiccid

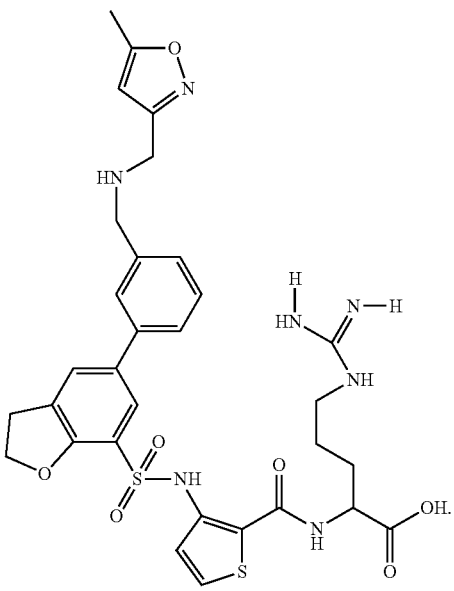

8. A compound of claim 5 comprising 5-guanidino-2-(3-(5-(3-(piperazin-1-ylmethyl)phenyl)-2,3-dihydrobenzofuran-7-sulfonamido)thiophene-2-carboxamido)pentanoic acid

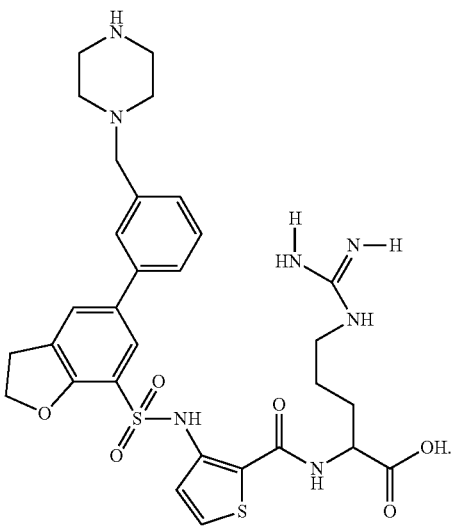

9. A compound of claim 5 comprising 5-guanidino-2-(3-(5-(3-((4-(methoxycarbonyl)piperidin-1-yl)methyl)phenyl)-2,3-dihydrobenzofuran-7-sulfonamido)thiophene-2-carboxamido) pentanoic acid

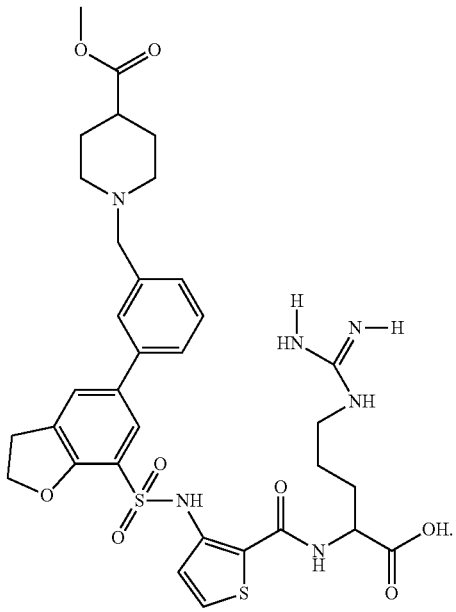

10. A compound of claim 5 comprising 1-(3-(7-(N-(2-(1-carboxy-4-guanidinobutylcarbamoyl)thiophen-3-yl)sulfamoyl)-2,3-dihydrobenzofuran-5-yl)benzyl)piperidine-4-carboxylic acid

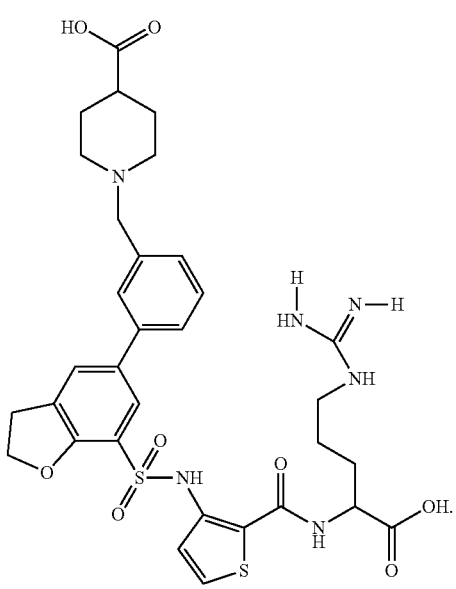

11. A compound of claim 5 comprising 2-(3-(5-(3-((4-(carboxymethyl)piperidin-1-yl)methyl)phenyl)-2,3-dihydrobenzofuran-7-sulfonamido)thiophene-2-carboxamido)-5-guanidinopentanoic acid

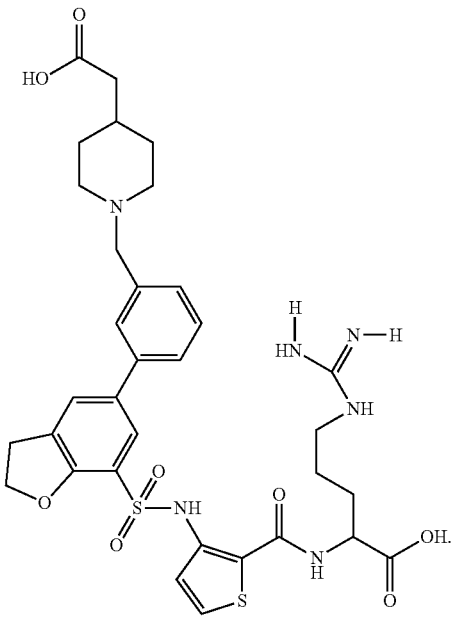

12. A compound of claim 5 comprising 5-guanidino-2-(3-(5-(2-((4-(methoxycarbonyl)piperidin-1-yl)methyl)phenyl)-2,3-dihydrobenzofuran-7-sulfonamido)thiophene-2-carboxamido) pentanoic acid

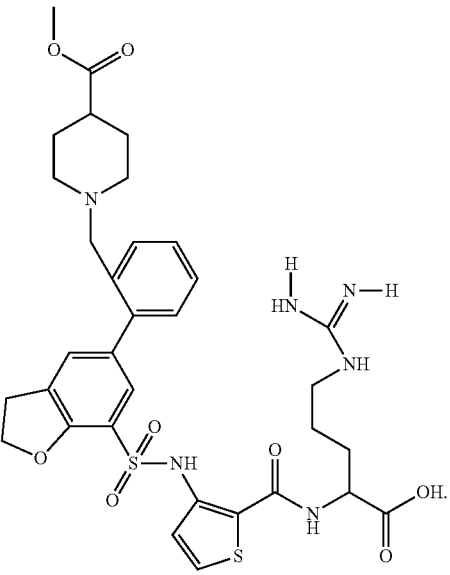

13. A compound of claim 5 comprising 1-(2-(7-(N-(2-(1-carboxy-4-guanidinobutylcarbamoyl)thiophen-3-yl)sulfamoyl)-2,3-dihydrobenzofuran-5-yl)benzyl)piperidine-4-carboxylic acid
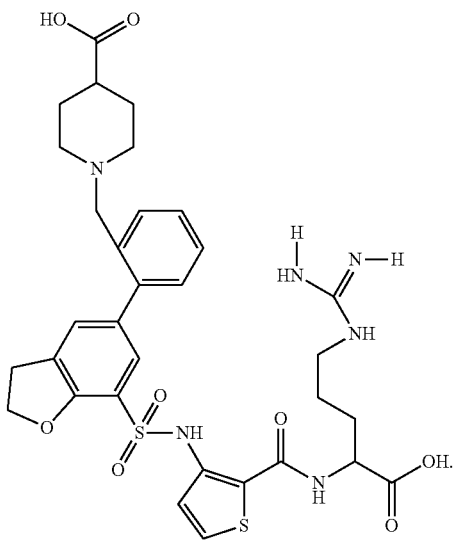
14. A compound of claim 5 comprising 5-guanidino-2-(3-(5-(2-((4-(2-oxopropyl)piperidin-1-yl)methyl)phenyl)-2,3-dihydrobenzofuran-7-sulfonamido)thiophene-2-carboxamido) pentanoic acid
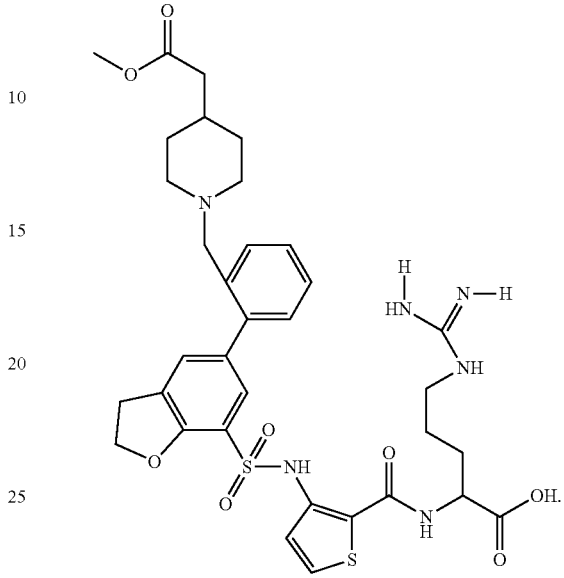
\* \* \* \* \*